(12) United States Patent
Yamazaki et al.

(10) Patent No.: US 9,574,870 B2
(45) Date of Patent: Feb. 21, 2017

(54) PROBE FOR OPTICAL IMAGING

(71) Applicant: NAMIKI SEIMITSU HOUSEKI KABUSHIKI KAISHA, Tokyo (JP)

(72) Inventors: Hiroshi Yamazaki, Kuroishi (JP); Eri Fukushima, Kuroishi (JP); Norikazu Sato, Kuroishi (JP); Tomoyuki Kugou, Kuroishi (JP); Takafumi Asada, Kuroishi (JP)

(73) Assignee: Namiki Seimitsu Houseki Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/018,322

(22) Filed: Feb. 8, 2016

(65) Prior Publication Data
US 2016/0153765 A1 Jun. 2, 2016

Related U.S. Application Data

(63) Continuation of application No. PCT/JP2013/081805, filed on Nov. 26, 2013.

(30) Foreign Application Priority Data

Aug. 10, 2013 (JP) .................................. 2013-167192

(51) Int. Cl.
G02B 6/26 (2006.01)
G01B 9/02 (2006.01)
A61B 5/00 (2006.01)

(52) U.S. Cl.
CPC ......... *G01B 9/02091* (2013.01); *A61B 5/0066* (2013.01); *A61B 5/0073* (2013.01);
(Continued)

(58) Field of Classification Search
CPC . G01B 9/02091; A61B 5/0073; A61B 5/6852; A61B 2562/228
(Continued)

(56) References Cited

U.S. PATENT DOCUMENTS 5,240,003 A * 8/1993 Lancee .................... A61B 8/12
310/162
6,687,010 B1 * 2/2004 Horii .................... G01B 9/0201
356/479
(Continued)

FOREIGN PATENT DOCUMENTS

JP 3885114 B2 2/2007
JP 2008-284340 A 11/2008
(Continued)

OTHER PUBLICATIONS

International Search Report; PCT/JP2013/081805; Jan. 28, 2014.
(Continued)

*Primary Examiner* — Sung Pak
(74) *Attorney, Agent, or Firm* — Studebaker & Brackett PC

(57) ABSTRACT

A probe for a three-dimensional (3D) scanning optical imaging which prevents rotational irregularity, axial runout, friction, rotation transmission delays of a rotational part by reducing occurrences of rotation transmission delays, torque loss, and the like, and can perform scanning of a certain length in an axial direction and obtain a three-dimensional observation image, in a probe for OCT image diagnosis. A fixed side optical fiber that transmits light between a tip side and a rear side of a probe and is non-rotatably disposed, a first optical path conversion means that rotates to emit a light ray in a substantially radial direction, a rotation side optical fiber which is rotated by a motor, and a second optical path conversion means that rotates and emits light toward the first optical path conversion means are collinearly disposed. In this way, it is possible to obtain a high quality 3D observation image.

12 Claims, 28 Drawing Sheets

(52) U.S. Cl.
CPC .......... *A61B 5/0084* (2013.01); *A61B 5/6852* (2013.01); *A61B 2562/228* (2013.01)

(58) Field of Classification Search
USPC .......................................................... 385/26
See application file for complete search history.

(56) References Cited

U.S. PATENT DOCUMENTS

| | | | | |
|---|---|---|---|---|
| 8,861,900 | B2* | 10/2014 | Bhagavatula | ........ A61B 5/0066 385/12 |
| 8,967,885 | B2* | 3/2015 | Bhagavatula | ........ G02B 6/2552 385/93 |
| 9,036,966 | B2* | 5/2015 | Bhagavatula | ............ G02B 6/32 385/33 |
| 2005/0143664 | A1* | 6/2005 | Chen | .................... A61B 5/6852 600/478 |
| 2009/0198125 | A1 | 8/2009 | Nakabayashi et al. | |
| 2010/0105980 | A1 | 4/2010 | Shimizu et al. | |
| 2015/0355413 | A1* | 12/2015 | Bhagavatula | ........ A61B 5/0066 385/26 |

FOREIGN PATENT DOCUMENTS

| | | |
|---|---|---|
| JP | 2009-201969 A | 9/2009 |
| JP | 4461216 B2 | 5/2010 |
| JP | 4520993 B2 | 8/2010 |
| JP | 2013-022414 A | 2/2013 |
| KP | 2010-200820 A | 9/2010 |

OTHER PUBLICATIONS

A Notice of Allowance issued by the Japanese Patent Office on Jun. 7, 2016, which corresponds to Japanese Patent Application No. 2015-531718 and is related to U.S. Appl. No. 15/018,322; with English language partial translation.

* cited by examiner

PROBE FOR OPTICAL IMAGING

TECHNICAL FIELD

The present invention relates to a probe for three-dimensional scanning optical imaging for three-dimensionally capturing and observing light reflected from a device under test in medical equipment or the like.

BACKGROUND ART

Image diagnostic technologies (optical imaging technologies) are technologies widely used for mechanical devices and medical treatment fields. For example, in a medical treatment field or a manufacturing field of precision instruments, schemes such as X-ray computed tomography (CT) capable of capturing a tomographic image or a three-dimensional (3D) tomographic image, nuclear magnetic resonance, an optical coherence tomography (OCT) image using coherency of light, in addition to general camera observation and ultrasonic diagnostic equipment have been researched and used as a means for image diagnosis. Referring to capturing of the tomographic image or the 3D tomographic image, the development of the OCT image diagnosis technology that obtains the most microscopic captured image has been recently drawing attention among the schemes.

The OCT image frequently uses a near infrared ray having a wavelength of about 1,300 nanometers (nm) as a light source, and the near infrared ray has non-invasiveness with respect to a living body, and has a shorter wavelength than that of an ultrasonic wave, and thus is excellent in spatial resolving power. In addition, since identification of about 10 micrometers (μm) [less than or equal to a ten of that of the ultrasonic diagnostic equipment] can be performed, the OCT image is expected to be used to detect, diagnose, and treat a diseased part in a gastric region, a small intestine region, and a blood vessel part of an arterial flow of a human body particularly in the medical treatment field by integrating the tomographic image scheme into an endoscope. For example, a representative configuration of an OCT endoscope to which this OCT image technology is applied is as indicated in Patent Document 1.

Incidentally, in the OCT endoscope indicated in Patent Document 1, as illustrated in FIG. 8 of the document, a torque of a motor is delivered to a rotating shaft through a belt, and delivered to a lens unit through a flexible shaft which passes through an optical sheath having a shape of a tube and includes an optical fiber or the like. For this reason, in some cases, abrasion powder has generated due to friction between an inner peripheral surface of the optical sheath and the flexible shaft. In addition, rotation speed unevenness, rotation transmission delay, variation of torque loss and the like have occurred due to friction, deflection, and torsion of the flexible shaft, elastic deformation of the belt or the like. Thus, an obtained analyzed image has been in disorder, and requested spatial resolving power has not been acquired. Further, even though a two-dimensional (2D) tomographic image illustrated in FIG. 26 of the document can be obtained using the configuration, a 3D image cannot be obtained using the configuration.

In addition, an OCT endoscope illustrated in Patent Document 2 corresponds to an OCT 3D image system in which a catheter having a shape of a long and thin tube is inserted into a circular guide catheter illustrated in FIG. 1 of the document, an optically-connected optical fiber or core which is rotatable and slidable is included in the catheter, and the optical fiber is driven to rotate and moved in a longitudinal direction as illustrated in FIG. 3 of the document to irradiate a body tissue, thereby observing an analyzed image. However, this configuration has a problem in that abrasion powder is generated due to friction between the inner peripheral surface of the catheter and an outer peripheral surface of a drive shaft. In addition, rotation speed unevenness, rotation transmission delay, change of torque loss, and the like have occurred due to friction, deflection, and torsion of the drive shaft, and thus an obtained analyzed image has been in disorder, and requested spatial resolving power has not been acquired.

In addition, in the invention disclosed in Patent Document 3, a reflecting mirror is directly connected to a tip of a rotating shaft of a motor illustrated in FIG. 2 of the document. However, in this configuration, even though a 2D tomographic image can be obtained using the reflecting mirror which rotates, a 3D image cannot be obtained.

CITATION LIST

Patent Document

Patent Document 1: JP 3885114 B1
Patent Document 2: JP 4520993 B1
Patent Document 3: JP 4461216 B1

SUMMARY OF THE INVENTION

Problem to be Solved by the Invention

The invention has been conceived in view of the above conventional circumstances, and an object of the invention is to implement a probe for optical imaging which prevents rotational irregularity, axial runout, friction, rotation transmission delay of a portion that rotates and emits a light ray by reducing occurrences of rotation transmission delay, torque loss, and the like, and which is capable of performing a scan of a certain length in an axial direction and obtaining a 3D observation image.

Means for Solving Problem

A means for solving the above-mentioned problem is a probe for optical imaging which guides light entering a tip side to a rear side. In the probe, a fixed side optical fiber which is non-rotatably disposed to transmit light between the tip side and the rear side of the probe and incorporated in a substantially tube-shaped catheter, a first optical path conversion means disposed on a tip side of the fixed side optical fiber and driven by a first motor to rotate, thereby emitting a light ray in a substantially radial direction, a rotation side optical fiber positioned between the fixed side optical fiber and the first optical path conversion means, optically connected by an optical rotary connector, and driven by a second motor to rotate, and a second optical path conversion means for rotating and emitting light toward a first rotating means by inclining an optical path to a tip side of the rotation side optical fiber by a minute angle with respect to a rotation center are collinearly disposed. 3D scanning is performed such that the second optical path conversion means changes an emission angle of a light ray in an axial direction while the first optical path conversion means emits the light ray in a radial direction.

Effect of the Invention

According to the invention, occurrences of rotation transmission delay, torque loss, and the like are reduced without friction of an optical fiber in a catheter of an endoscope device or the like. Further, it is possible to obtain a three-dimensional (3D) observation image having high spatial resolving power in an OCT endoscope by independently rotating a first optical path conversion means and a second optical path conversion means to intentionally change an emission angle of a light ray in both a substantially radial direction and a central axis direction.

MODE(S) FOR CARRYING OUT THE INVENTION

Figure 1:
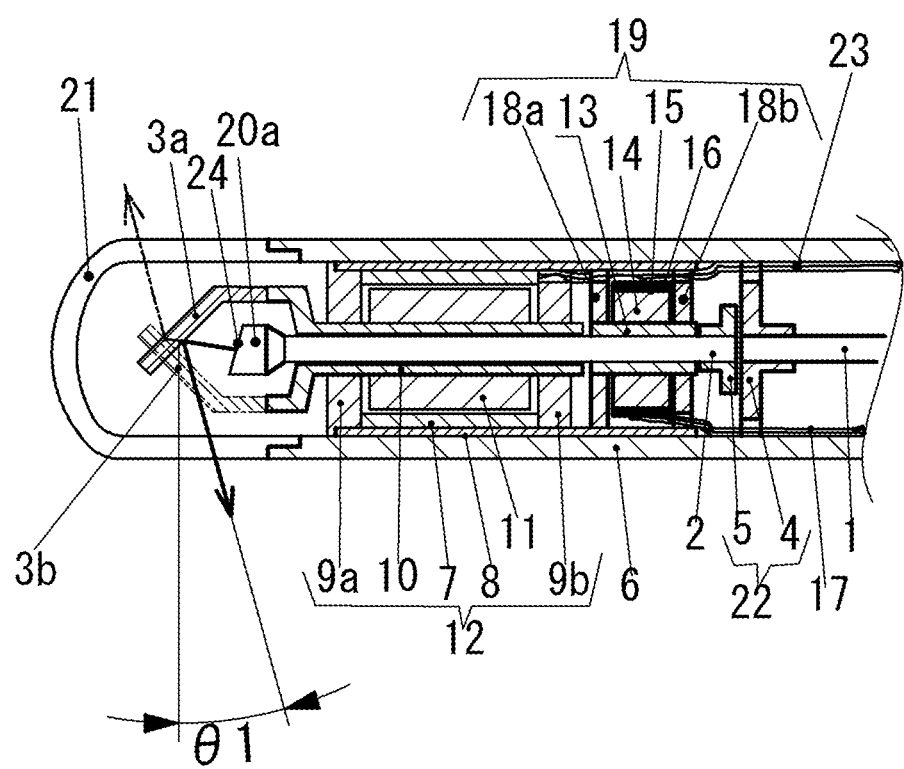
FIG. 1 is a cross-sectional view illustrating a probe for optical imaging according to a first embodiment of the invention.

According to a first characteristic of a probe for three-dimensional (3D) scanning-type optical imaging of the present embodiment, in a probe for optical imaging which guides light entering a tip side to a rear side, a fixed side optical fiber non-rotatably disposed to transmit light between the tip side and the rear side of the probe, a first optical path conversion means disposed on a tip side of the fixed side optical fiber and driven by a first motor to rotate, thereby emitting a light ray in a substantially radial direction, a rotation side optical fiber positioned between the fixed side optical fiber and the first optical path conversion means, optically connected by an optical rotary connector, and driven by a second motor to rotate, and a second optical path conversion means which rotates and emits light toward the first optical path conversion means by inclining an optical path to a tip side of the rotation side optical fiber by a minute angle with respect to a rotation center are collinearly disposed.

According to this configuration, when the first optical path conversion means rotates to two-dimensionally and radially reflect a light ray sent to the rotation side optical fiber through the fixed side fiber from a rear side, and the second optical path conversion means rotates to change an angle with respect to the rotation center to an emission direction of the light ray, it is possible to conduct 3D observation and to obtain a 3D observation image having high spatial resolving power.

According to a second characteristic, a rotating shaft of the first motor has a hollow shape, the first optical path conversion means is fixed thereto, and the rotation side optical fiber relatively rotatably penetrates into a hollow hole, and a rotating shaft of the second motor has a hollow shape, and the rotation side optical fiber is fixed to a hole corresponding to the hollow shape and rotated.

According to this configuration, since the first motor and the second motor may be disposed on a rear side with respect to the first optical path conversion means, wires of the motors are not present on a tip side of the first optical path conversion means. Therefore, a light ray is not blocked by the wires, and thus it is possible to emit light in a 360° direction and to obtain a perfect 3D observation image without missing.

According to a third characteristic, the first motor is positioned on a tip side with respect to the first optical path conversion means, the first optical path conversion means is attached to a rotating shaft thereof, the rotating shaft of the second motor has a hollow shape, and the rotation side optical fiber is fixed to a hole corresponding to the hollow shape and rotated.

According to this configuration, the first motor is not required to have a hollow shaft, and thus can have a smaller diameter. Accordingly, it is possible to configure a thin probe for endoscopes.

According to a fourth characteristic, at least one of the first motor and the second motor is an ultrasonic motor using piezoelectric elements or electrostrictive elements, a rotating shaft rotatably penetrates into a center hole provided substantially at a center of a substantially polygonal columnar vibrator, the center hole of the vibrator has a slit portion extending toward an outer circumference, a laminar piezoelectric element having an electrode is stuck to an outer peripheral surface of the vibrator, and voltages are successively applied such that rotational vibrations are generated independently from the piezoelectric element on one side of the slit and the piezoelectric element on the opposite side of the slit, thereby driving the rotating shaft to rotate.

According to this configuration, a spring force is generated between the vibrator and the rotating shaft to generate a stable frictional force by including the slit in the vibrator, and rotational vibration is generated such that mirroring is performed on both sides of the slit using a slit surface as a boundary by independently applying voltages to respective piezoelectric elements on both sides of the slit surface. Therefore, a sufficiently great torque may be generated using a small vibrator to drive and rotate the first or second optical path conversion means, and thus it is possible to obtain an endoscope probe that acquires a compact 3D observation image having high spatial resolving power.

According to a fifth characteristic, the first optical path conversion means which is driven and rotated by the first motor includes a substantially planar mirror having an angle of inclination with respect to a rotation center.

According to this configuration, it is possible to configure the first optical path conversion means to be compact, exhibit a sufficiently high reflectance, and obtain a compact 3D observation image having high spatial resolving power.

According to a sixth characteristic, the first optical path conversion means is a rotatable mirror, and the reflecting surface is a cylindrical surface.

According to this configuration, it is possible to obtain a 3D observation image in a wider range in an axial direction.

According to a seventh characteristic, the second optical path conversion means which is driven and rotated by the second motor includes a prism having a substantially planar surface that is very slightly inclined from a rotation center.

According to this configuration, it is possible to configure the second optical path conversion means to be compact, exhibit a sufficiently high transmittance and light concentrating efficiency of a light ray, and obtain a compact 3D observation image having high spatial resolving power.

According to an eighth characteristic, the second optical path conversion means is a prism having a substantially spherical surface inclined to a tip.

According to this configuration, the second optical path conversion means may exhibit a sufficiently high transmittance and light concentrating efficiency of a light ray, and a compact 3D observation image having high spatial resolving power may be obtained.

According to a ninth characteristic, there is provided the probe for optical imaging according to any one of claims 1 to 8, in which the optical rotary connector has a first cover covering an outer circumference of at least one of the fixed side optical fiber and the rotation side optical fiber with a minute gap interposed therebetween and a second cover covering the first cover with a minute gap interposed therebetween, a thread groove is formed on a cylindrical surface coming into contact with the minute gap of at least one of the first cover and the second cover, and a transparent optical fluid is injected into the minute gap.

According to this configuration, a transparent fluid is prevented from flowing out, leaking and permeating, attenuation of a light ray is reduced in an optical rotary connector, and it is possible to obtain a 3D observation image having high spatial resolving power.

According to a tenth characteristic, the optical rotary connector is configured by allowing end surfaces of the fixed side optical fiber and the rotation side optical fiber to face each other with a minute distance therebetween, and injecting a transparent fluid into a gap formed by the fixed side optical fiber, the rotation side optical fiber, a bearing of the second motor, and a rotating shaft of the second motor.

According to this configuration, optical loss in the optical rotary connector is minimized, and a satisfactory 3D image is obtained.

According to an eleventh characteristic, the probe for optical imaging includes a first pulse generating means for generating at least one pulse per rotation according to a rotation angle of the first motor, and a second pulse generating means for generating at least one pulse per rotation according to a rotation angle of the second motor, the probe for optical imaging includes a control means for adjusting rotation speeds of the first motor and the second motor by pulses from the first pulse generating means and the second pulse generating means, and the first motor and the second motor are rotated by setting a relation between a rotation speed N1 of the first motor and a rotation speed N2 of the second motor to N2=N1−X [rotations/second] such that a light ray is emitted in a substantially radial direction at a rotation speed of N1 [rotations/second] from the first optical path conversion means, and an emission angle of the light ray is changed in an axial direction at a speed of X [reciprocations/second].

According to this configuration, it is possible to change an emission angle in an axial direction at a slow speed of X reciprocations per second (for example, 1 reciprocation/second) while emission of a light ray rotates at a high speed of N1 (for example, 30 rotations/second) to helically emit the light ray, it is possible to efficiently collect 3D data, and it is possible to obtain an endoscope probe that acquires a 3D observation image having high spatial resolving power.

According to a twelfth characteristic, the first motor and the second motor are rotated at the same rotation speed by the control means by receiving pulses from the first pulse generating means and the second generating means such that the first motor and the second motor are in a stand-by state, and rotation per minute is changed by generation of a start signal such that a relation between the rotation speed N1 of the first motor and the rotation speed N2 of the second motor corresponds to N2=N1−X [rotations/second].

According to this configuration, it is possible to immediately start 3D scanning simultaneously with the start signal.

Next, preferred embodiments of the invention will be described with reference to drawings.

Embodiment 1

FIGS. 1 to 8 illustrate Embodiment 1 of a probe for optical imaging according to the invention.

FIG. 1 is a cross-sectional view illustrating a probe for 3D scanning-type optical imaging according to Embodiment 1 of the invention. A fixed side optical fiber 1 which guides a light ray from a rear end side to a tip side of the probe is inserted into a hole of a sufficiently long catheter 6 having a shape of a tube, and is fixed by an optical fiber fixture 4.

A rotation side optical fiber 2 is rotatably provided on a tip side of the fixed side optical fiber 1. First optical path conversion means 3a and 3b including mirrors having planar shapes are rotatably attached to a tip of the rotation side optical fiber 2 independently from the rotation side optical fiber 2 by a first motor 12, and configured to emit light rays in a whole circumferential direction by being rotated.

In addition, a second optical path conversion means 20 is attached to the tip of the rotation side optical fiber 2. The second optical path conversion means 20 concentrates a light ray penetrating the fixed side optical fiber 1 and emits the light ray toward the first optical path conversion means 3a and 3b with a slight angle in a tip direction while being rotated.

The rotation side optical fiber 2 and the fixed side optical fiber 1 are spaced apart by a minute distance of about 5 μm to face each other, and included in an optical rotary connector 22 together with a rotating douser 5 and the optical fiber fixture 4. Further, a high transmittance may be maintained between the rotation side optical fiber 2 and the fixed side optical fiber 1, and the rotation side optical fiber 2 and the fixed side optical fiber 1 are optically connected to each other with little loss.

In the first motor 12, a motor coil 7 and first bearings 9b and 9a are fixed to a motor case 8, and a hollow rotating shaft 10 to which a rotor magnet 11 is attached rotates. A voltage is applied to the motor coil 7 from an electric wire 23, and the first optical path conversion means 3 is attached to the hollow rotating shaft 10.

Figure 2:
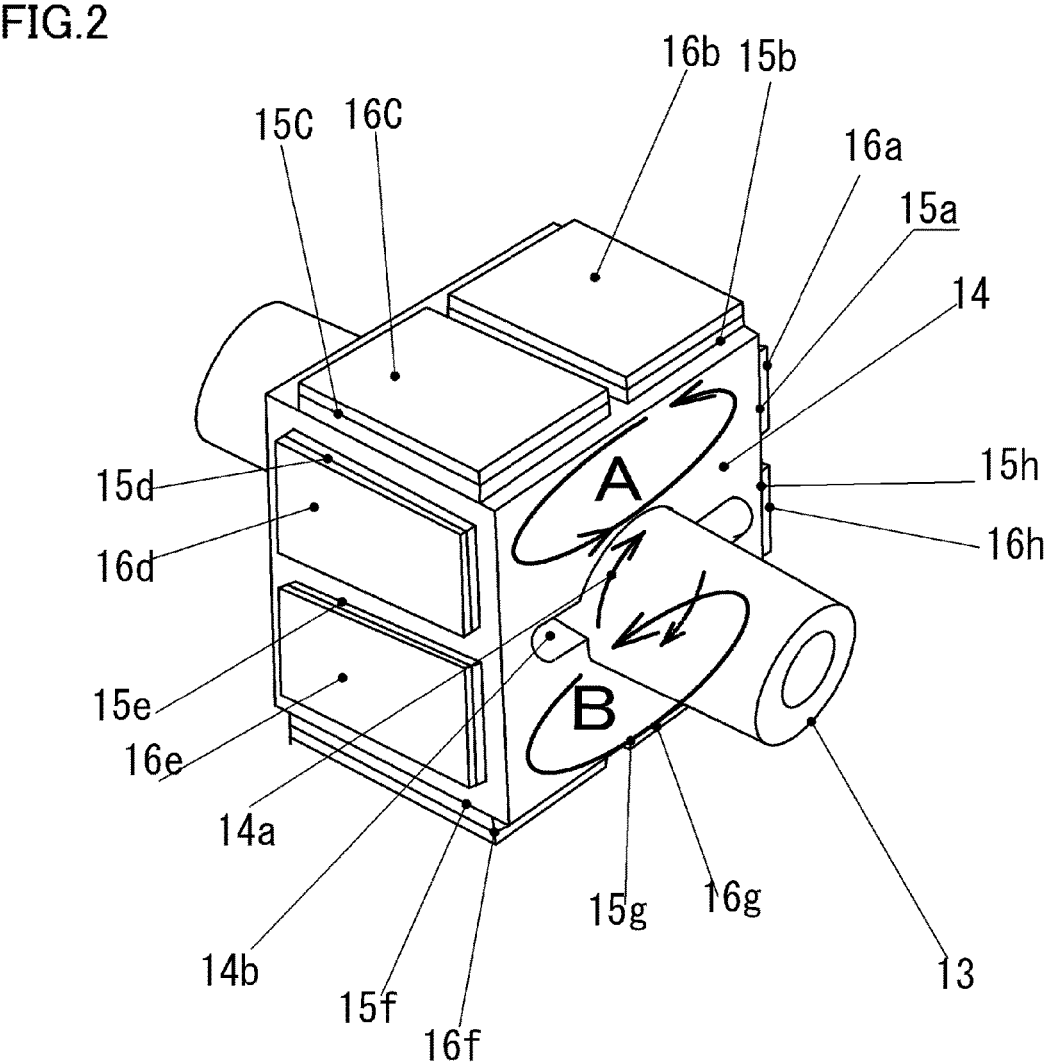
FIG. 2 is a diagram illustrating a configuration of a second motor of the probe for optical imaging.

In a second motor 19, second bearings 18a and 18b are attached to the motor case 8 to rotatably impede a second rotating shaft 13. Referring to FIG. 2, the second rotating shaft 13 is lightly press-fitted to a hole 14a formed substantially at a center of a vibrator 14. However, a slit 14b is provided to be connected to the hole 14a, and thus a stable frictional force is generated between the vibrator 14 and the second rotating shaft 13 due to a characteristic of a spring of the vibrator 14.

Electrostrictive elements 15a, 15b, 15c, 15d, 15e, 15f, 15g, and 15h are stuck to an outer circumference of the vibrator 14, and electrodes 16a, 16b, 16c, 16d, 16e, 16f, 16g, and 16h are formed on the electrostrictive elements. The respective electrodes are wired by an electric wire 17 illustrated in FIG. 1, and voltages are applied thereto. Rotation of the vibrator 14 is stopped with respect to the second bearings 18a and 18b. In some cases, the electric wire 17 may simply function as a rotation stopper.

Referring to FIG. 1, a light-transmitting part 21 capable of transmitting a light ray is attached to the catheter 6 near an outer circumference of the first optical path conversion means 3 that emits a light ray. The light-transmitting part 21 is made of a transparent resin, glass, or the like, and coated as necessary to reduce surface reflection and enhance transmittance of a light ray.

Figure 7:
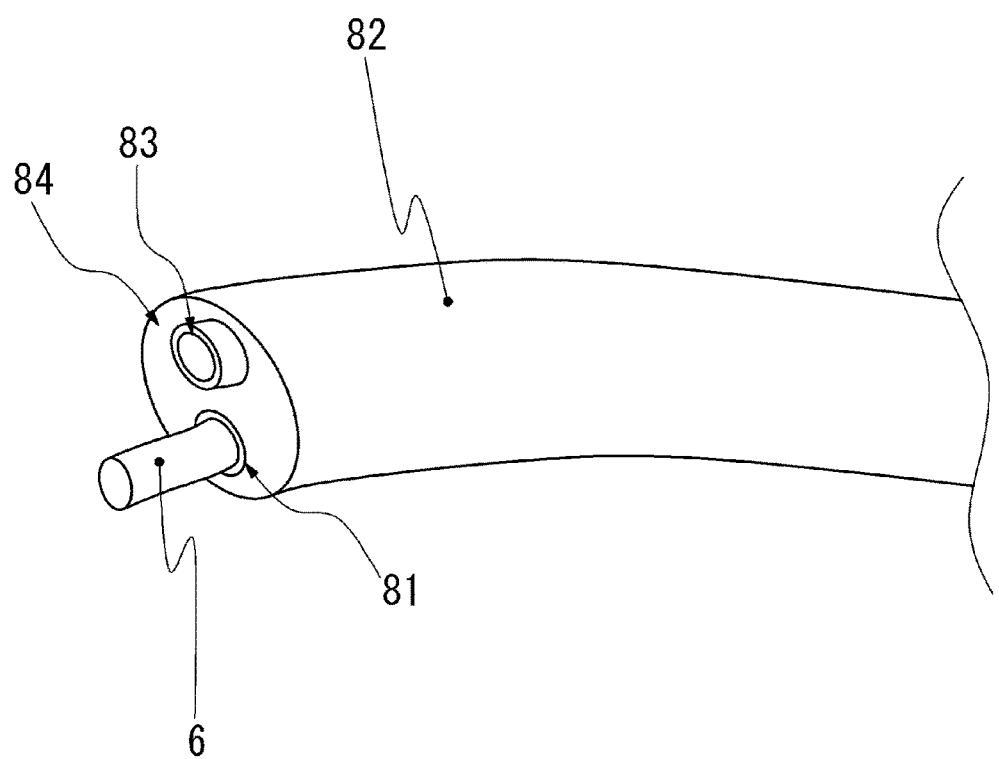
FIG. 7 is a diagram for a description of a guide catheter using the probe for optical imaging.

FIG. 7 is a diagram for a description of a guide catheter 82 using the probe for 3D scanning-type optical imaging. The guide catheter 82 is configured to have a diameter of about 9 mm or less so as to be inserted into a gastric region, a small intestine, and a bronchus of a human body, and have appropriate strength and flexibility of fluorine resin or the like.

In addition, the catheter 6 is configured to have a diameter of 10 mm or less, and similarly configured as a strong and flexible fluorine resin tube such that a pinhole is not formed. Further, a distal end observation portion 84 thereof includes a CCD camera unit 83, and a communication hole referred to as a forceps channel 81 is formed over the entire length of the guide catheter 82. The catheter 6 of the probe for optical imaging of the invention is configured to be freely inserted into and removed from the forceps channel.

Figure 8:
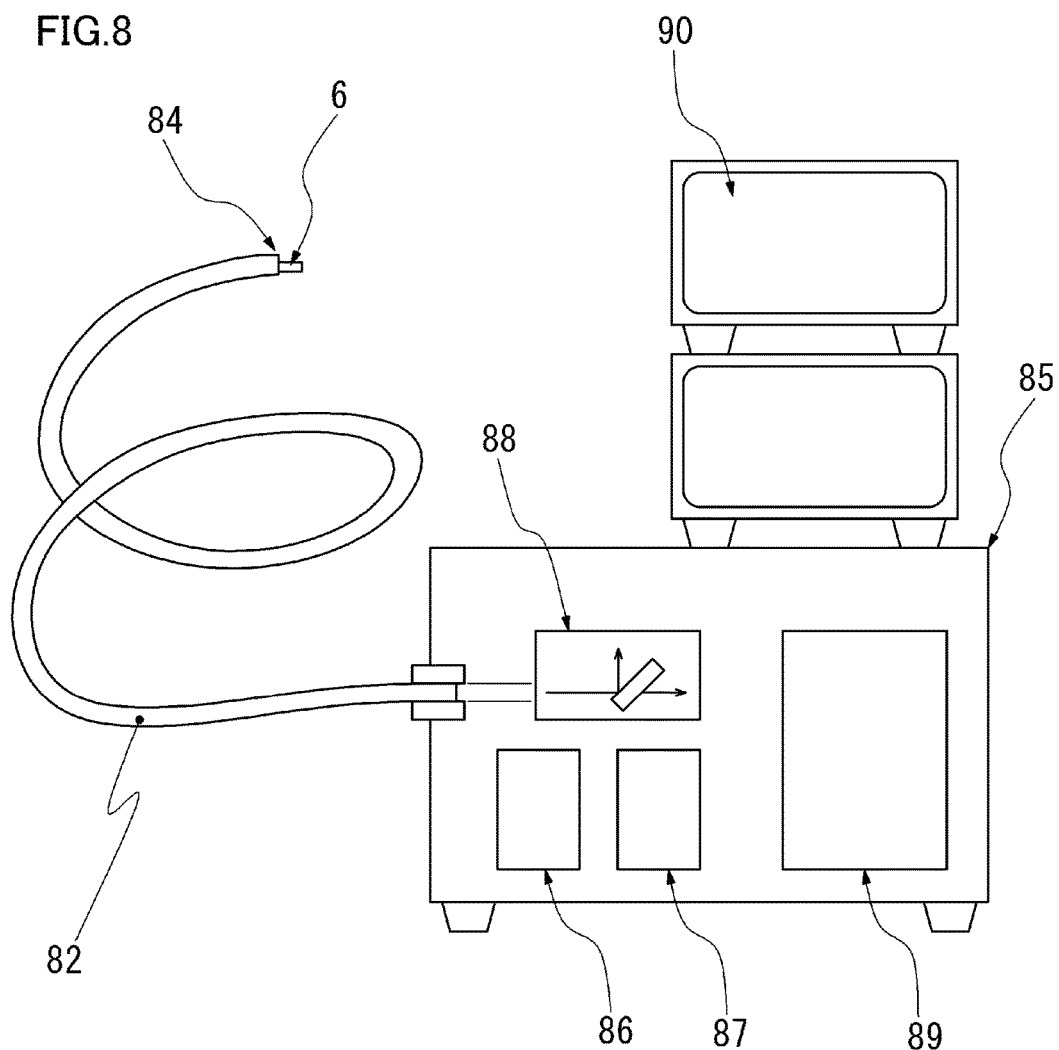
FIG. 8 is a diagram illustrating a configuration of an endoscope imaging apparatus using the probe for optical imaging.

FIG. 8 is a diagram illustrating a configuration of an endoscope device using the probe for 3D scanning-type optical imaging. The catheter 6 is attached to a main body 85 of an OCT endoscope device together with the guide catheter 82. The main body includes a first motor driver circuit 86 of the motor 12, a driver circuit 87 of the second motor 19, an optical interference analyzer 88, and an image analysis computer 89. An image of the CCD camera unit 83 and an OCT 3D image analyzed and created by the computer 89 are displayed on a monitor 90.

The first motor 12 of FIG. 1 is driven to rotate by being supplied with power from the first motor driver circuit 86 of FIG. 8, and the second motor 19 is driven to rotate by being supplied with a voltage from the second motor driver circuit 87.

The fixed side optical fiber 1 and the rotation side optical fiber 2 penetrating into the catheter 6 illustrated in FIG. 1 are bendable glass fibers, which have diameters within a range of about 0.2 to 0.4 mm.

The second optical path conversion means 20 illustrated in FIG. 1 is configured as a conical, cylindrical prism, or the like having a substantially flat portion 24 that reflects a light ray, and polished to have surface roughness and form accuracy greater than or equal to those of a general optical component such that reflectance is enhanced.

A hole of the hollow rotating shaft 10 illustrated in FIG. 1 has a diameter within a range of 0.2 mm to 0.5 mm. The hollow rotating shaft 10 contains metal or ceramics as a material, and has a hollow shape through a drawing process using a mold of a molten metal or extruding using a mold of ceramics before firing. After a hardening treatment, an outer peripheral surface is subjected to finishing processing by a polishing method or the like.

Next, with regard to the probe for 3D scanning optical imaging of FIGS. 1 to 8 described above, characteristic effect thereof will be described in detail.

Referring to FIG. 8, a light ray such as a near-infrared ray emitted from a light source in the main body 85 travels through an inside of the fixed side optical fiber 1 in the catheter 6 on the inside of the guide catheter 82.

Referring to FIG. 1, even though power is supplied from the electric wire 23, and the first motor 12 rotates at a constant speed within a range of about 1,800 to 20,000 rpm, a guided light ray is emitted from the second optical path conversion means 20a by passing through the optical rotary connector 22 and the rotation side optical fiber 2, reflected from the substantially flat portion 24 of the first optical path conversion means 3a, and rotated and emitted in a direction changed to a certain angular direction (an angle of θ1 in FIG. 1).

The light ray corresponding to the near infrared ray further passes through the light-transmitting part 21, and penetrates an outer layer of a skin of a human body up to a depth within a range of 2 to 5 mm. The light ray reflected therefrom is guided to the optical interference analyzer 88 in an opposite direction of the same optical path as that described above by passing through the light-transmitting part 21 ⇒ the first optical path conversion means 3a ⇒ the second optical path conversion means 20a ⇒ the rotation side optical fiber 2 ⇒ the optical rotary connector 22 ⇒ the fixed side optical fiber 1.

Figure 3:
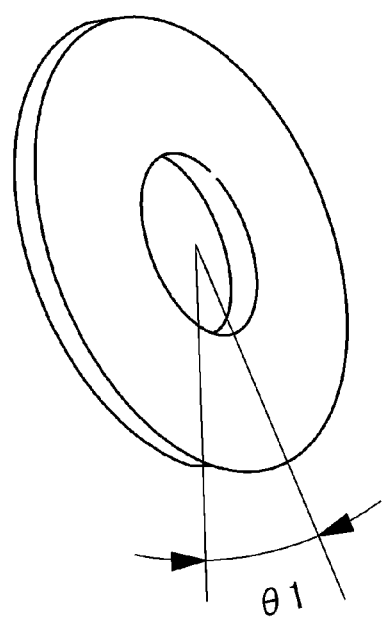
FIG. 3 is a diagram for a description of a range of rotary scanning of the probe for optical imaging.

In this instance, an emission range of the light ray, that is, a scanning range of the optical interference endoscope in which the light ray penetrates covers up to a distance which two-dimensionally corresponds to a radius within a range of about 2 to 5 mm as illustrated in FIG. 3. Referring to FIG. 1, the first optical path conversion means 3a and 3b correspond to two representative rotating positions indicated by a solid line and a dashed line.

Next, when voltages are applied to the arranged electrodes 16a, 16b, 16c, and 16d of the second motor 12 of FIG. 2 in order through the electric wire 17 from the second motor driver circuit 87 illustrated in FIG. 8, and voltages are applied to the arranged electrodes 16e, 16f, 16g, and 16h in order on an opposite side of the slit 14b at the same time, the vibrator 44 simultaneously generates two rotary traveling waves in directions A and B indicated by arrows in FIG. 2.

The rotary traveling waves apply torques to a surface of the second rotating shaft 13 from both directions such that the rotation side optical fiber 2, the douser 5, and second optical path conversion means 20 are slowly rotated. The second motor is an ultrasonic vibration motor which slowly rotates such that the motor rotates once for several seconds. In addition, the vibrator 44 having the slit 14b may not have an integral structure. For example, the vibrator 44 may be configured by stacking a plurality of steel sheets.

Figure 4:
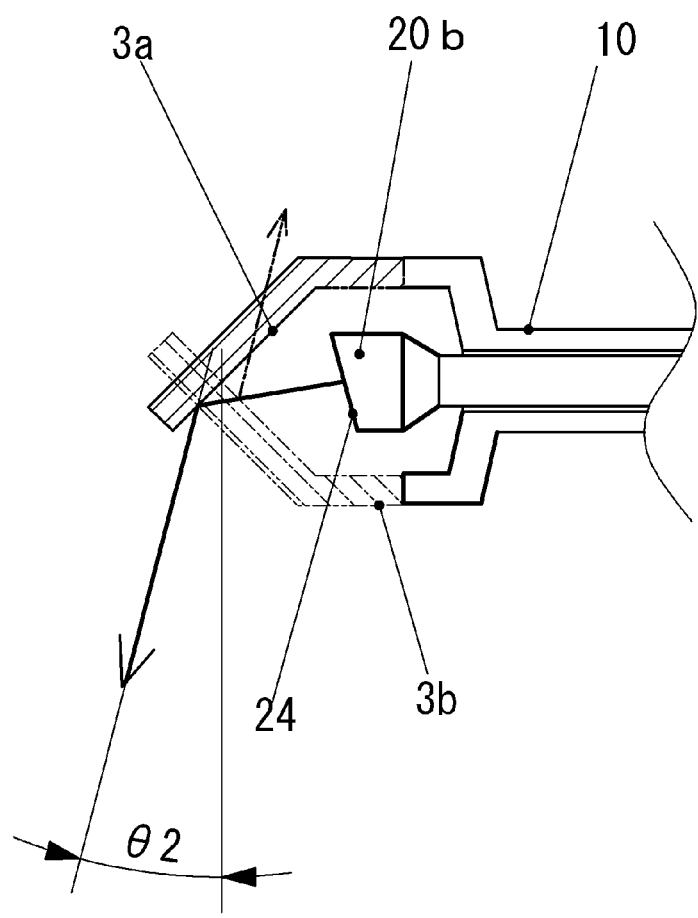
FIG. 4 is a diagram for a description of a second optical path conversion means of the probe for optical imaging.
Figure 5:
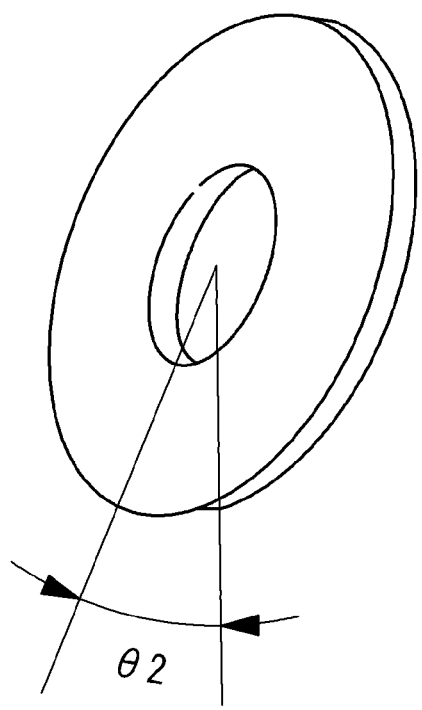
FIG. 5 is a diagram for a description of a range of rotary scanning of the probe for optical imaging.

Subsequently, as illustrated in FIG. 4, when the second optical path conversion means rotates and moves to a position 20b, the light ray is reflected from the rotating first optical path conversion means 3a and 3b, and a path of the light ray is changed by a certain angle corresponding to θ2 in the drawing. In this instance, an emission range of the light ray is a 2D range which is inclined as illustrated in FIG. 5.

Figure 6:
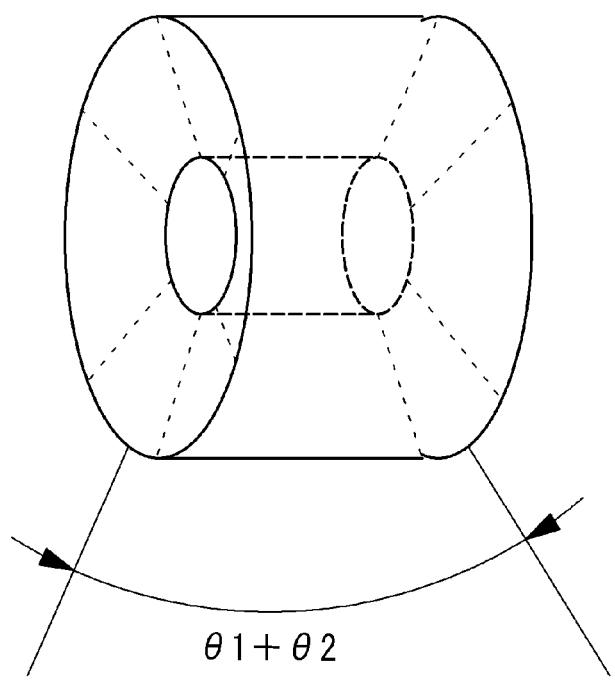
FIG. 6 is a diagram for a description of a range of three-dimensional (3D) scanning of the probe for optical imaging.

Then, when the second optical path conversion means 20 slowly rotates once, an emission direction of the light ray is gradually changed in a range of θ1 to θ2, and thus the emission range of the light ray becomes a range of θ1+θ2 as illustrated in FIG. 6, thereby performing 3D radiation.

In addition, even though scanning is performed around a whole circumference of 360° by rotating the first optical path conversion means 3, a signal line and an electric wire need not to be provided within the scanning range of 360°, and thus it is possible to obtain a clear OCT image of 360° without missing.

Embodiment 2

Next, a description will be given of Embodiment 2 of a probe for 3D scanning-type optical imaging related to the invention (see FIGS. 9 and 10).

Figure 9:
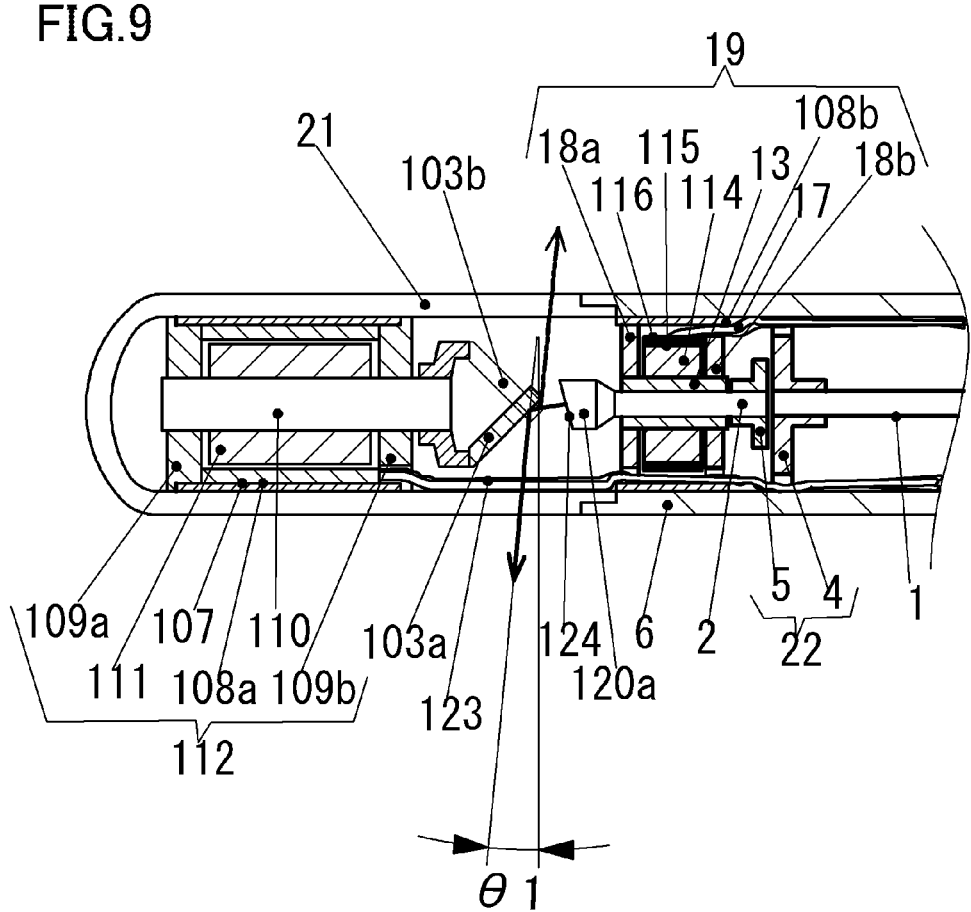
FIG. 9 a cross-sectional view illustrating a probe for optical imaging according to a second embodiment of the invention.

In the probe for 3D scanning-type optical imaging according to Embodiment 2 illustrated in FIG. 9, a fixed side optical fiber 1 having a length sufficient to connect a tip side to a rear side is fixed by an optical fiber fixture 4 on an inside of an internal diameter of a substantially tube-shaped catheter 6.

A sufficiently short rotation side optical fiber 2 is configured on the same axis as that of the fixed side optical fiber 1 on the tip side of the fixed side fiber 1, and a second optical path conversion means 120 is integrally included in a tip side of the rotation side optical fiber 2 and slowly rotated by a second motor 19 that has a second rotating shaft 13 on the same axis as that of the rotation side optical fiber 2.

The rotation side optical fiber 2, a douser 5, the fixed side optical fiber 1, and the optical fiber fixture 4 form an optical rotary connector 22. Further, the fixed side fiber 1 and the rotation side optical fiber 2 are spaced apart from each other by a slight distance of about several tens of μm. However, cross sections of the respective fibers are processed to be right angles and smooth, and positioned on the same axis. Thus, a light ray may pass between the two fibers without attenuation.

On a tip side of the second optical path conversion means 120, a first optical path conversion means 103, including a substantially planar mirror or the like, is attached to a first motor 112 and rotates.

In the first motor 112, a motor coil 107 and first bearings 109a and 109b are attached to a thin walled and cylindrical motor case 108a, and the first bearings 109a and 109 rotate and support a first rotating shaft 110 and a rotor magnet 111, and rotate the first optical path conversion means 103 by being supplied with power by an electric wire 123.

In addition, second bearings 18a and 18b are attached to a motor case 108b, and the second bearings 18a and 18b support the second rotating shaft 13. The second rotating shaft 13 is inserted into or lightly press-fitted to a hole of a vibrator 114 including a surface to which an electrostrictive element 115 on which a pattern electrode 116 is formed is stuck. The second rotating shaft 13 is included in the second motor 19 together with an electric wire 17.

Figure 10:
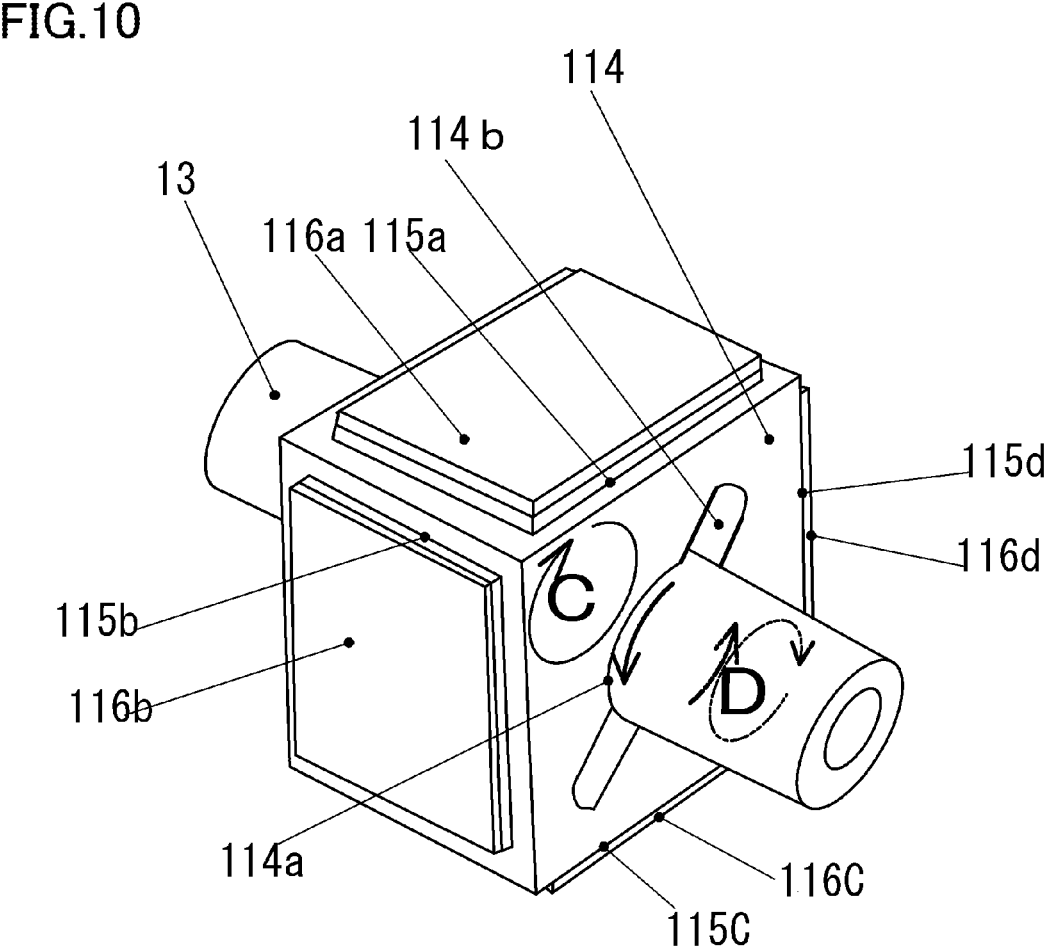
FIG. 10 is a diagram illustrating a configuration of a second motor of the probe for optical imaging.

Referring to FIG. 10, in the second motor 19, the second rotating shaft 13 is press-fitted to a hole 114a, and electrostrictive elements 115a and 115b are stuck to sides of the vibrator 114 using a slit 114b as a boundary. Electrodes 116a and 116b are formed on the respective electrostrictive elements 115a and 115b.

In addition, electrostrictive elements 115c and 115d are stuck to opposite sides with respect to the slit 114b, and electrodes 116c and 116d are formed thereon. When a voltage is applied from the electric wire 17 in an order of the electrodes 116b→116a to generate a rotary traveling wave indicated by an arrow C of the drawing, and a voltage is applied in an order of electrodes 116d→116c, a rotary traveling wave indicated by an arrow D in the drawing is generated. The second rotating shaft 13 receives torques resulting from the rotary traveling waves from two directions, and slowly rotates the rotation side optical fiber 2 and the second optical path conversion means 120.

In Embodiment 2, an operation and a merit are nearly the same as those of Embodiment 1 illustrated in FIG. 1, and a light ray is emitted in a direction of θ1 of FIG. 9 and emitted through a transmission portion 21. A range in which a light ray is emitted by rotations of the first motor 112 and the second motor 19 corresponds to the range illustrated in FIG. 6 similarly to Embodiment 1 of FIG. 1.

Referring to FIG. 9, the first rotating shaft 110 is not a hollow shaft, and thus may be made thinner. Therefore, the first motor 112 may be configured to be thin.

In the present embodiment, the fixed side optical fiber 1 is fixed and does not rotate in an inside of the catheter 6 over a whole length from a rear to a tip, and thus is not rubbed. Therefore, occurrences of rotation transmission delay, torque loss, and the like are reduced, rotation speed unevenness of the first optical path conversion means 103 is excluded, and high spatial resolving power of 10 μm is obtained.

Furthermore, when an electric current is applied to the second motor 19 to intentionally change an emission angle of the second optical path conversion means 120, a direction of a light ray emitted from the first optical path conversion means may be changed to perform 3D scanning. Thus, it is possible to obtain a clear OCT 3D observation image having high spatial resolving power. However, in the present embodiment, the electric wire 123 of the first motor 112 interferes with 360° scanning, and a portion of an image signal may be missing.

Embodiment 3

Next, a description will be given of Embodiment 3 of a probe for 3D scanning-type optical imaging related to the invention (see FIGS. 11 to 15).

Figure 11:
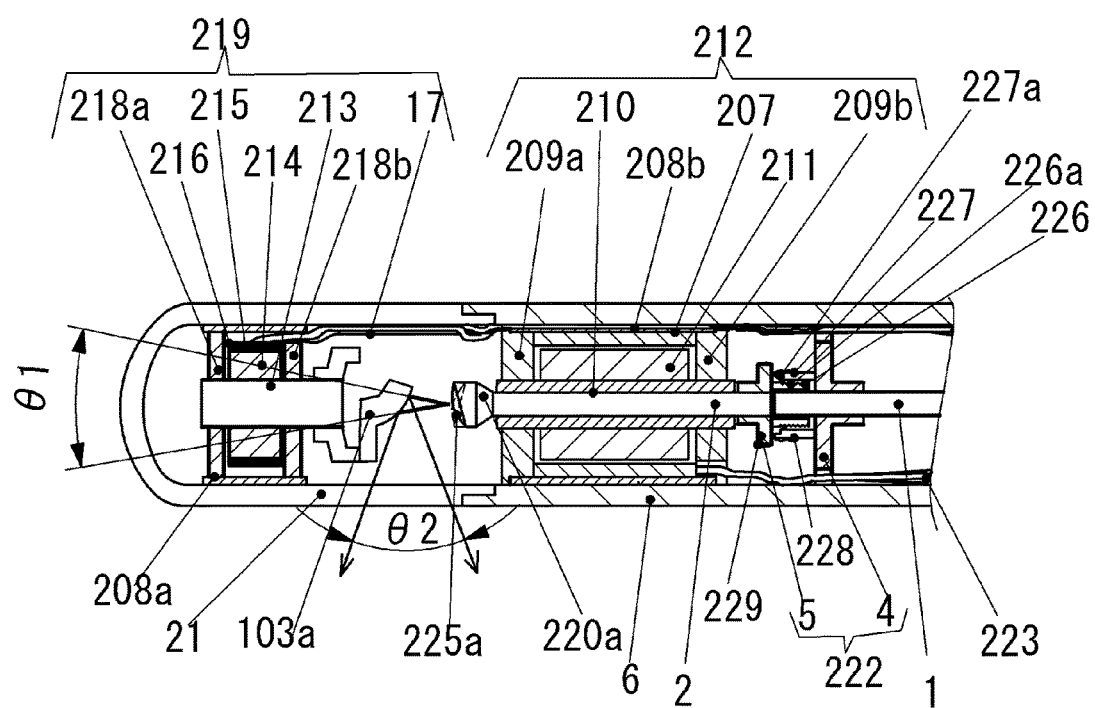
FIG. 11 a cross-sectional view illustrating a probe for optical imaging according to a third embodiment of the invention.

In the probe for 3D scanning-type optical imaging according to Embodiment 3 illustrated in FIG. 11, a fixed side optical fiber 1 having a length sufficient to connect a tip side to a rear side is fixed by an optical fiber fixture 4 on an inside of a substantially tube-shaped catheter 6. The fixed side optical fiber 1, a rotation side optical fiber 2, the optical fiber fixture 4, and a douser 5 are included in an optical rotary connector 222.

The rotation side optical fiber 2 which is sufficiently short is configured on the same axis as that of the fixed side optical fiber 1 on the tip side of the fixed side fiber 1, and a second optical path conversion means 220 including, for example, a cylindrical prism or a sphero-prism is integrally included in a tip side of the rotation side optical fiber 2. A light ray is rotated and emitted from the second optical path conversion means 220 at a slight angle with respect to a shaft center.

A rotatable first optical path conversion means 103 having, for example, a mirror is included in a tip side of the second optical path conversion means 220 to receive a light ray emitted from the second optical path conversion means, reflect the light ray in a substantially orthogonal direction, and rotate and emit the light ray toward a whole circumference through a light-transmitting part 21.

The first optical path conversion means is driven by a first motor 219 to rotate at a slow speed of one revolution per about 0.5 second to several seconds. The first motor 219 includes a motor case 208a, a first rotating shaft 213, a vibrator 214, an electrostrictive element 215, an electrode 216, an electric wire 17, and first bearings 218a and 218b, and an operation thereof is the same as that of the second motor 19 of Embodiment 2.

The second optical path conversion means is driven by a second motor 212 to rotate at a speed of about 1,800 rpm to 20,000 rpm. The second motor 219 includes a motor case 208b, a motor coil 207, second bearings 209a and 209b, a second rotating shaft 210, a rotor magnet 211, and an electric wire 223, and an operation thereof is the same as that of the first motor 112 of Embodiment 2.

Figure 12:
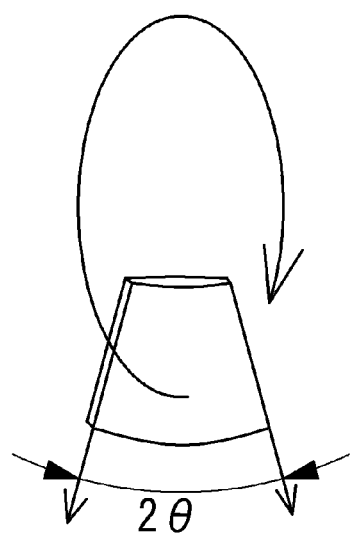
FIG. 12 is a diagram for a description of a range of rotary scanning of the probe for optical imaging.

Referring to FIG. 11, a reflecting surface of the first optical path conversion means 103 is a cylindrical surface. When a light ray rotated and emitted from the first optical path conversion means 220 at an angle indicated by θ1 in the drawing is reflected from the cylindrical surface of the first optical path conversion means 103, an emission angle is greater than θ1. The light ray is emitted in a 2D range as illustrated in FIG. 12 at an angle wider than θ2 of the drawing.

Figure 13:
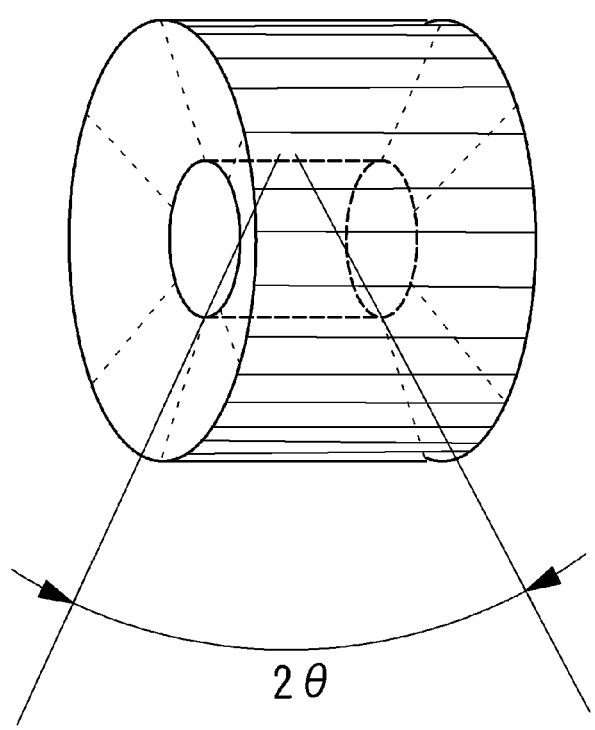
FIG. 13 is a diagram for a description of a range of 3D scanning of the probe for optical imaging.

Next, when the first optical path conversion means 219 slowly rotates once, a light ray is three-dimensionally emitted as illustrated in FIG. 13, and a 3D image is obtained.

A surface shape of a substantially spherical surface portion 225 of the second optical path conversion means 220 is appropriately designed in accordance with a shape of the reflecting surface of the first optical path conversion means. When the shape corresponds to a substantially spherical shape or has a minute curved surface when compared to a flat surface, light is excellently concentrated in terms of optics, and an observation image of an endoscope is improved in some cases.

Figure 15:
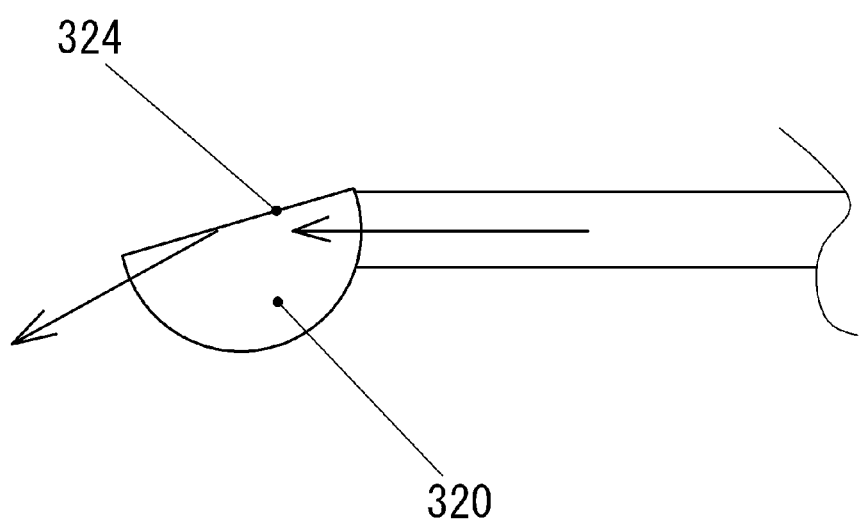
FIG. 15 is a diagram for a description of a second optical path conversion means of the probe for optical imaging.

In addition, referring to FIG. 11, the second optical path conversion means may correspond to a second optical path means having a spherical surface as illustrated in FIG. 15, and have a reflecting surface 324.

Figure 14:
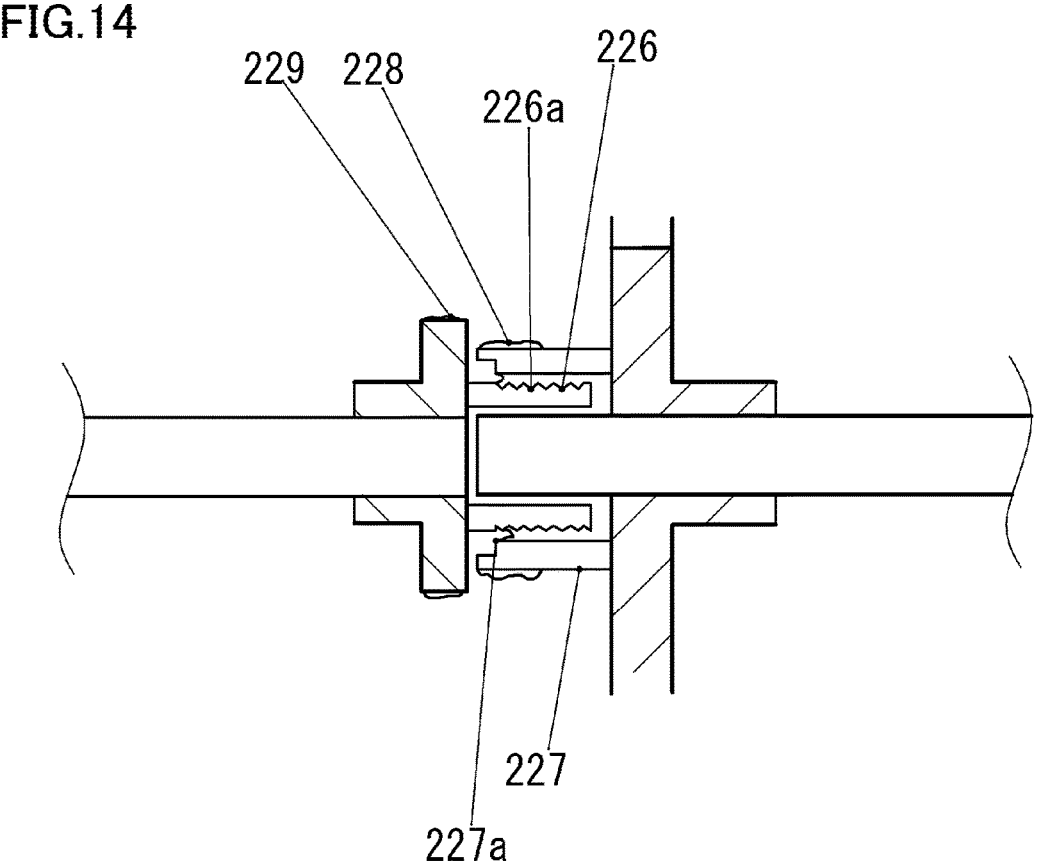
FIG. 14 is a cross-sectional view illustrating an optical rotary connector of the probe for optical imaging.

FIG. 14 is a cross-sectional view of the optical rotary connector 222. An outer circumference of at least one of the fixed side optical fiber 1 and the rotation side optical fiber 2 is covered with a first cover 226 with a minute radial clearance interposed therebetween, an outer circumference thereof is further covered with a second over 227 with a minute radial clearance interposed therebetween, one of the first cover 226 and the second cover 227 is fixed to a rotating douser, and the other one is fixed to a non-rotating optical fiber fixture.

The two minute radial clearances are within a range of about 10 μm to 30 μm, and silicone oil or a fluorinated optical fluid 230 is injected into the clearances. In this way, opposite surfaces of the fixed side optical fiber 1 and the rotation side optical fiber 2 are filled with the optical fluid 230. Therefore, a transmittance therebetween is enhanced, optical loss of an OCT observation device is extremely small, and image performance is enhanced.

A thread groove is formed on at least one surface of the two minute clearances on cylindrical surfaces of the first and second covers 226 and 227, and the optical fluid 230 may be sealed and confined in the clearances due to a similar effect to that of a screw pump through rotation. In addition, an outer peripheral surface of the second cover 227 and a surface of the douser 5 may be coated with barrier layers 228 and 229, thereby preventing the optical fluid 230 from being exuded to the outside.

An oil reservoir 227a is provided near an opening of the second cover 227. An adequate amount of the optical fluid 230 is applied to the oil reservoir 227a in a step in which the optical rotary connector is assembled, and then put into a depressing vessel, thereby discharging internal air and allowing the optical fluid 230 to permeate into the inside.

In the present embodiment, the fixed side optical fiber 1 is not rotated in an inside of the long catheter 6 over a whole length from a rear to a tip of the catheter 6, and thus is not rubbed. Therefore, it is possible to prevent occurrences of rotation transmission delay, torque loss, and the like.

Embodiment 4

FIGS. 16 to 24 illustrate Embodiment 4 of a probe for optical imaging according to the invention.

Figure 16:
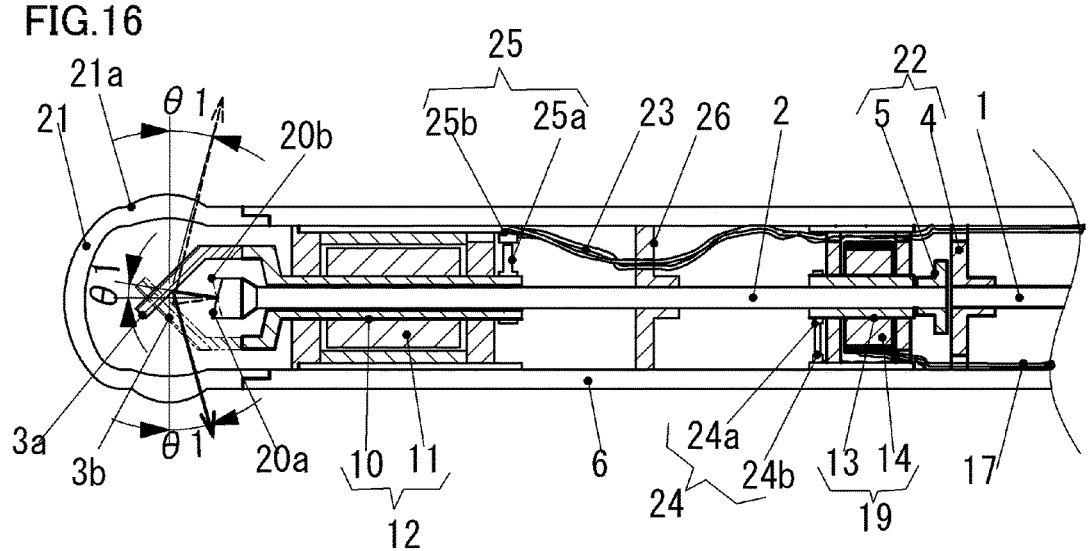
FIG. 16 is a cross-sectional view illustrating a probe for optical imaging according to a fourth embodiment of the invention.
Figure 17:
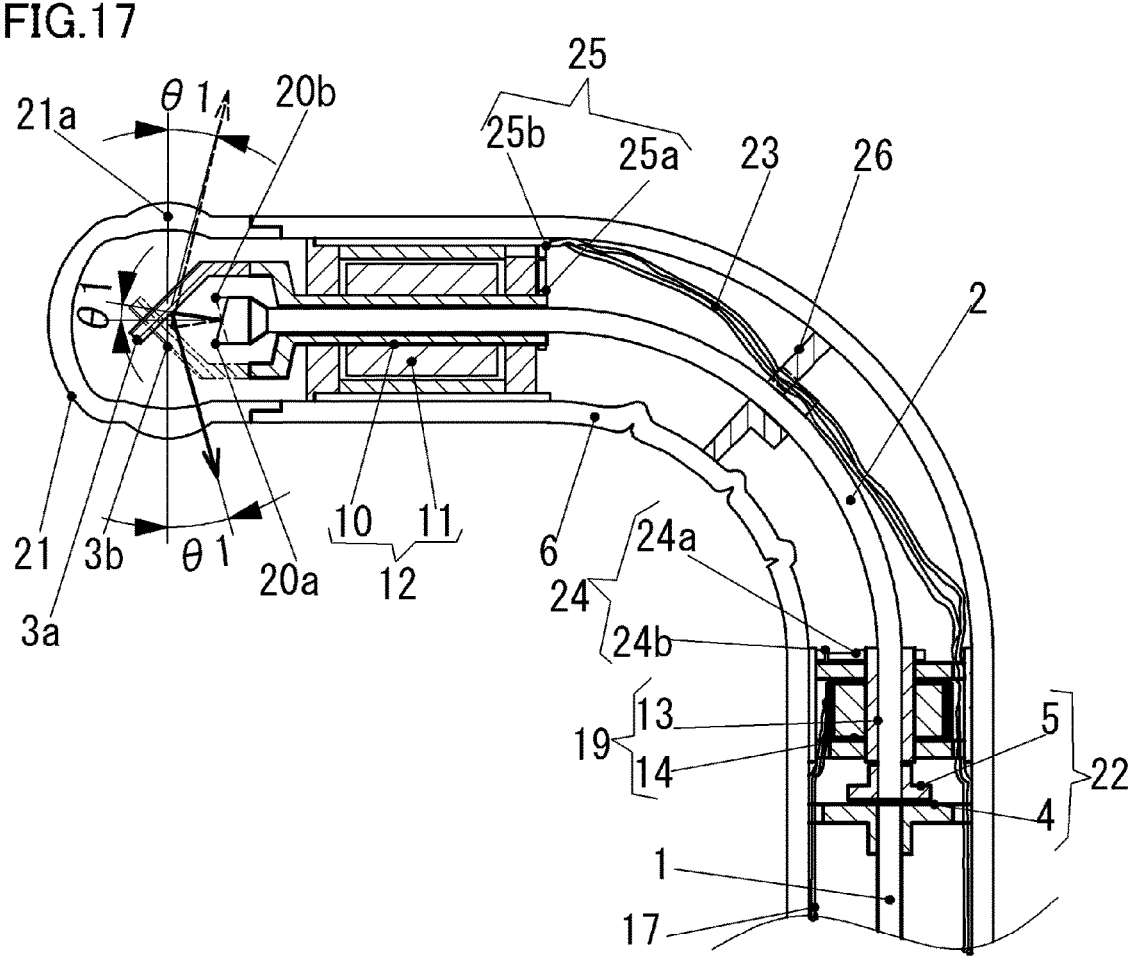
FIG. 17 is a cross-sectional view illustrating a curved probe for optical imaging.

FIGS. 16 and 17 are cross-sectional views of a probe for 3D scanning-type optical imaging according to Embodiment 4 of the invention. FIG. 16 illustrates the probe for optical imaging arranged on a straight line, and FIG. 17 illustrates the probe for optical imaging in a state in which a tip end portion is bent. A fixed side optical fiber 1 which guides a light ray from a rear end side to a tip side of the probe is inserted into substantially a center on the inside of a sufficiently long catheter 6 having a shape of a tube.

A rotation side optical fiber 2 is rotatably provided on a tip side of the fixed side optical fiber 1. The rotation side optical fiber 2 is rotatably supported by an optical fiber guide bearing 26, and a first optical path conversion means 3 including a substantially planar mirror and the like is rotatably attached to a tip of the rotation side optical fiber 2 independently of the rotation side optical fiber 2 by the first motor 12, and is configured to emit a light ray, for example, in a whole circumferential direction at an angle of θ1 in the drawing by being rotated. The first optical path conversion means 3 is indicated by reference numerals 3a and 3b in the drawing depending on rotation angle thereof.

In addition, a second optical path conversion means 20 is attached to the tip of the rotation side optical fiber 2. The second optical path conversion means 20 concentrates a light ray penetrating the fixed side optical fiber 1 and emits the light ray toward the first optical path conversion means 3 with a slight angle in a tip direction while being rotated. The second optical path conversion means 20 is indicated by reference numerals 20a and 20b in the drawing depending on rotation angle thereof.

The rotation side optical fiber 2 and the fixed side optical fiber 1 are spaced apart by a minute distance of about 5 μm to face each other, and included in an optical rotary connector 22 together with a rotating douser 5 and an optical fiber fixture 4. Further, a high transmittance may be maintained between the rotation side optical fiber 2 and the fixed side optical fiber 1, and the rotation side optical fiber 2 and the fixed side optical fiber 1 are optically connected to each other with little loss.

The first motor 12 is incorporated in the catheter 6, and a hollow rotating shaft 10 to which a rotor magnet 11 is attached rotates. A voltage is applied to the first motor 12 through an electric wire 23, and the first optical path conversion means 3 is attached to the hollow rotating shaft 10 to rotate.

In a second motor 19, a second rotating shaft 13 is lightly press-fitted to a hole formed substantially in a center of a vibrator 14, and a stable frictional force is generated between the second rotating shaft 13 and the vibrator 14 by elasticity or spring characteristic of the vibrator 14. The second rotating shaft 13 of the second motor 19 is fixed to a center hole of the rotation side optical fiber 2, a voltage is applied through a wired electric wire 17, and the second optical path conversion means 20 is rotated.

Figure 18:
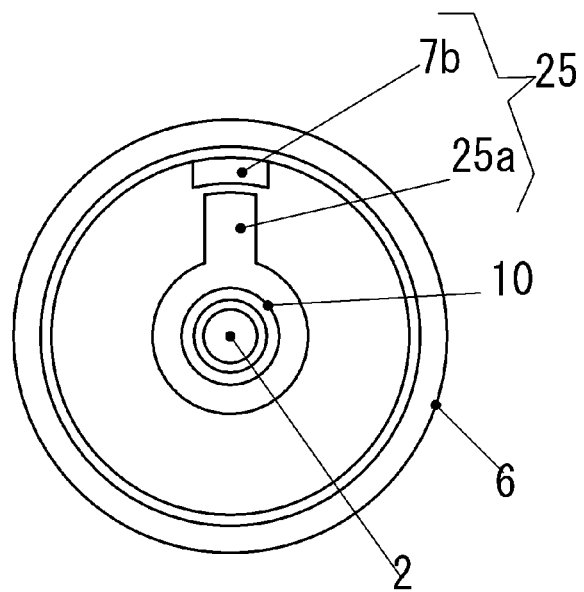
FIG. 18 is a diagram for a description of a pulse generating part of a first motor of the probe for optical imaging.
Figure 19:
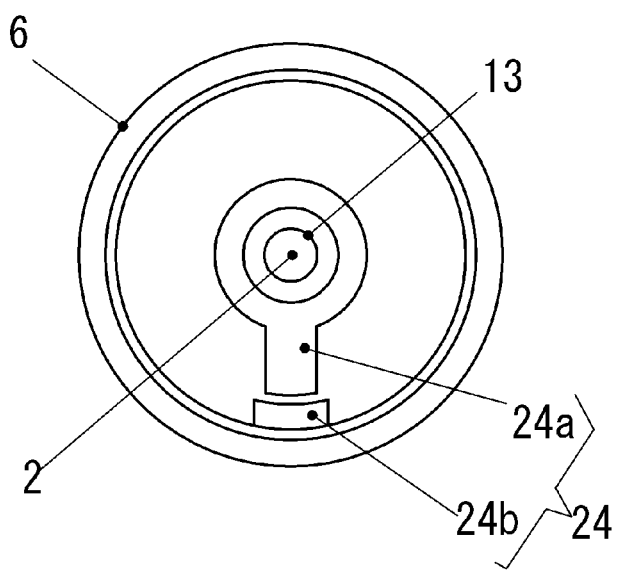
FIG. 19 is a diagram for a description of a pulse generating part of a second motor of the probe for optical imaging.

The first motor 12 is provided with a first pulse generating means 25 including a rotation side part 25a and a fixed side part 25b illustrated in FIG. 18. Similarly, the second motor 19 is provided with a second pulse generating means 24 including a rotation side part 24a and a fixed side part 24b illustrated in FIG. 19. Each of the first pulse generating means 25 and the second pulse generating means 24 generates one or a plurality of pulse signals per rotation according to rotation angles of the first and second motors. A magnetic sensor, such as an inductive coil or a hall element, or an optical sensor configured by an optical shutter and a light sensor is used in a pulse generation principle.

A light-transmitting part 21 capable of transmitting a light ray is attached to the catheter 6 near an outer circumference of the first optical path conversion means 3 that emits a light ray as necessary. A substantially spherical surface portion 21a is formed on the light-transmitting part 21 as necessary. The substantially spherical surface portion 21a is formed such that an angle at which a near-infrared ray enters the light-transmitting part does not change much even when an angle (θ1 in the drawing) at which the near-infrared ray is emitted gradually changes. In addition, a thickness thereof is changed rather than being fixed as necessary. The light-transmitting part 21 is made of a transparent resin, glass, or the like, and coated as necessary to reduce surface reflection, minimize total reflection of a light ray, and enhance transmittance.

The first motor 12 of FIG. 16 is driven to rotate by being supplied with power from the first motor driver circuit 86 of FIG. 8, and the second motor 19 is driven to rotate by a voltage supplied from the second motor driver circuit 87. In addition, a rotation speed of the first motor 12 may be adjusted by a pulse signal from the first pulse generating means 25, and a rotation speed of the second motor 19 may be adjusted to a value set in advance by a pulse signal from the second pulse generating means 24.

Next, a detailed description will be given of a characteristic effect of the probe for 3D scanning-type optical imaging of FIGS. 16 to 24 described above.

Referring to FIGS. 7 and 8, a light ray such as a near-infrared ray emitted from a light source in the main body 85 travels through an inside of the fixed side optical fiber 1 in the catheter 6 on the inside of the guide catheter 82.

Figure 22:
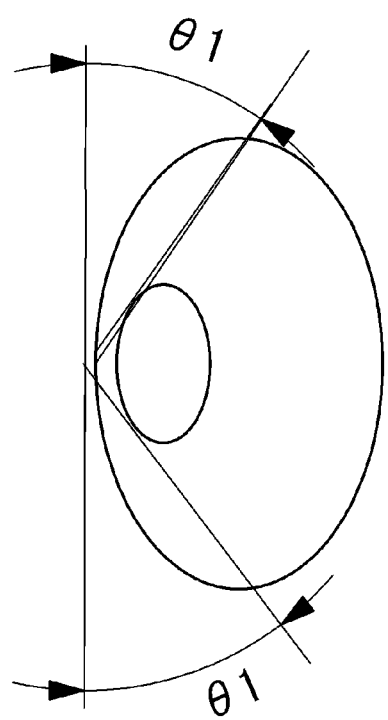
FIG. 22 is a diagram for a description of a range of rotary scanning of the probe for optical imaging.

Referring to FIG. 16, even though power is supplied from the electric wire 23, and the first motor 12 rotates at a constant speed within a range of about 1,800 to 20,000 rpm, a light ray guided from the fixed side optical fiber 1 is emitted from the second optical path conversion means 20a by passing through the optical rotary connector 22 and the rotation side optical fiber 2, reflected from the substantially flat portion of the first optical path conversion means 3a, and rotated and emitted in a direction changed to a certain angular direction (a downward angle of θ1 indicated by a solid arrow in FIG. 16). In addition, when the first optical path conversion means 3 and the second optical path conversion 20 are rotated at the same rotation speed and shifted to positions indicated by reference numerals 3b and 20b in the drawing, a light ray is emitted from the second optical path conversion means 20b, reflected from a substantially flat portion of the first optical path conversion means 3b, and rotated and emitted in a direction changed to a certain angular direction (an upward angle of θ1 indicated by a dashed arrow in FIG. 16). In this instance, the light ray is emitted in a substantially conical shape indicated by an angle θ1 as illustrated in FIG. 22 to scan a device under test.

Figure 20:
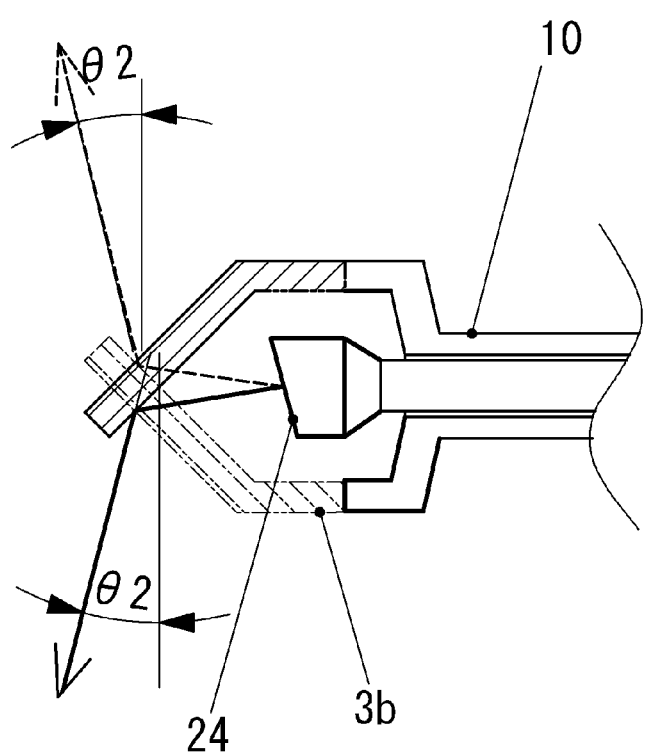
FIG. 20 is a diagram for a description of a first and second optical path conversion means of the probe for optical imaging.
Figure 23:
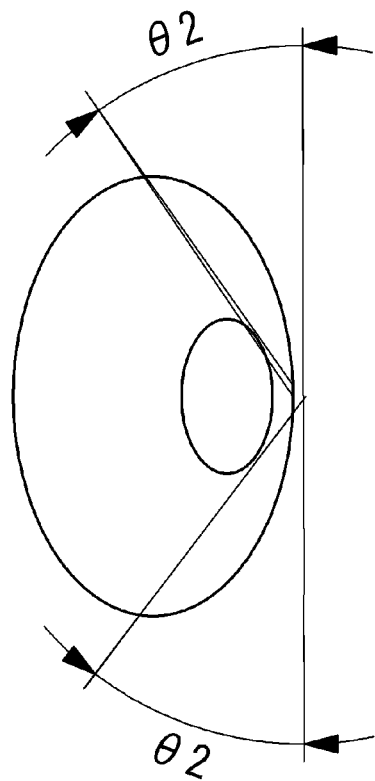
FIG. 23 is a diagram for a description of a range of rotary scanning of the probe for optical imaging.

FIG. 20 is a diagram corresponding to a case in which phase angles of the first optical path conversion means 3 and the second optical path conversion 20 are different from each other by 180 degrees when compared to FIG. 16. This state is generated when the first optical path conversion means 3 and the second optical path conversion 20 rotate at rotation speeds. A light ray guided from the fixed side optical fiber 1 is emitted from the second optical path conversion means 20b of FIG. 20 by passing through the optical rotary connector 22 and the rotation side optical fiber 2, reflected from the substantially flat portion of the first optical path conversion means 3a, and rotated and emitted in a direction changed to a certain angular direction (a downward angle of θ2 indicated by a solid arrow in FIG. 20). In this instance, the light ray is emitted in a substantially conical shape indicated by an angle θ2 as illustrated in FIG. 23 to scan a device under test. In this way, when the first optical path conversion means 3 and the second optical path conversion 20 are rotated by minutely changing different rotation speeds thereof, it is possible to change an emission angle of a light ray from the angle θ1 indicated in FIGS. 16 and 22 within a range of the angle θ2 indicated in FIGS. 20 and 23.

Figure 24:
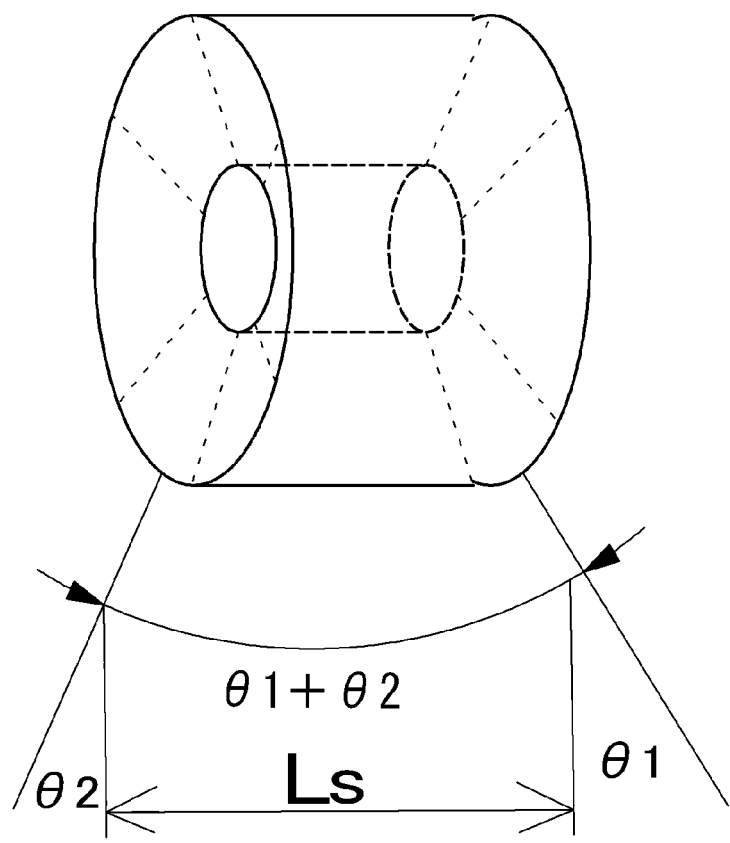
FIG. 24 is a diagram for a description of a range of 3D scanning of the probe for optical imaging.

In this way, an emission angle of a light ray is repeated within a range of θ1 to θ2 in FIG. 24, and a probe for endoscopes may three-dimensionally scan a tested part within a range of a hollow cylinder. An external diameter of the scanned hollow cylinder is within a range of about 2 mm to 10 mm, and a length in the axial direction, which is indicated by Ls in the drawing, of a range scanned once by the probe for optical imaging of the invention is within a range of about 2 mm to 10 mm.

The light ray corresponding to the near-infrared ray further passes through the light-transmitting part 21 of FIG. 16, and penetrates an outer layer of a skin of a human body up to a depth within a range of 2 mm to 5 mm. The light ray reflected therefrom is guided to the optical interference analyzer 88 by passing through the light-transmitting part 21 the first optical path conversion means 3 ⇒ the second optical path conversion means 20 ⇒ the rotation side optical fiber 2 ⇒ the optical rotary connector 22 ⇒ the fixed side optical fiber 1.

Figure 21:
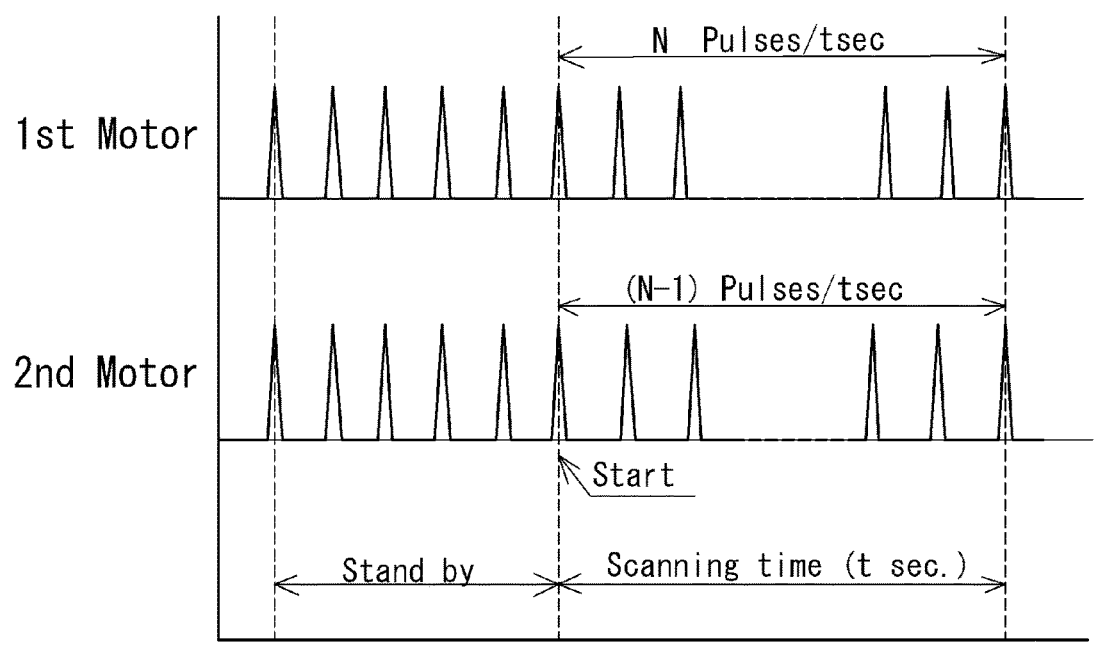
FIG. 21 is a timing chart of motor pulses of the probe for optical imaging.

FIG. 21 is a timing chart of generated pulses of the first motor 12 and the second motor 19 of the probe for optical imaging of the invention. An upper chart in the drawing illustrates a generated pulse from the first pulse generating means 25 of the first motor 12, and a lower chart in the drawing illustrates a generated pulse from the second pulse generating means 24 of the second motor 19. A horizontal axis indicates a time axis.

A period of time indicated by "stand-by" in the drawing corresponds to a state in which the first motor 12 and the second motor 19 wait for scanning start signals while rotating at the same revolutions per minute.

Next, in response to a "start signal" being output by an operator that operates the probe for imaging, the first motor 12 rotates at a speed (for example, 30 rotations/second) indicated by N pulses/second and starts to store OCT observation image data of a device under test in a computer 89.

Simultaneously, the second motor 19 rotates at a speed of, for example, (N−1) pulses/second (for example, 29 rotations/second). Thus, as illustrated in FIG. 24, an emission angle changes from θ1 up to θ2 for 0.5 second and returns to the angle of θ1 again after 1 second, and 3D emission of the light ray is completed.

In this case, a computer fetches 3D data two times (2 times correspond to 1 set) within a period of time at which the emission angle reciprocates between θ1 and θ2, and obtains a clear 3D OCT diagnosis image without missing. When data is fetched and stored, the first motor 12 and the second motor 19 are in the "stand-by state" again, and rotated while waiting for subsequent "start signals".

A more practical method of using an OCT probe for 3D scanning of the invention is as below. For example, in a first step, the probe of the invention is fed into a long blood vessel. In this case, while the first motor 12 and the second motor 19 rotate at the same revolutions per minute, the probe of the invention continuously performs 2D 360° scanning to specify a position of a diseased part near a blood vessel in a human body from a 2D image displayed on a monitor 90.

The 2D image is fetched using a pulse signal from the first pulse generating means 25, 25a, and 25b of FIG. 16 as a trigger and is displayed on the monitor 90 by processing of the computer.

Next, in a second step, pushing and pulling of the probe are suspended, the catheter 6 is stopped, and the second motor 19 is rotated at a speed of, for example, (N−1) pulses/second (for example, 29 rotations/second) to three-dimensionally emit a light ray. An OCT apparatus may display a 3D image having high spatial resolving power on the monitor 90 to closely observe a diseased part.

The 3D image is fetched to the computer 89 using an instance, at which pulse signals from the first pulse generating means 25, 25a, and 25b and pulse signals from the second pulse generating means 24, 24a, and 24b are simultaneously output, as a trigger, and is displayed on the monitor 90.

In a third step, the probe of the invention is further shifted to another end portion. In this case, while the first motor 12 and the second motor 19 rotate at the same revolutions per minute, the probe of the invention continuously performs 2D 360° scanning, and displays a 2D OCT image on the monitor 90.

In the present embodiment, on an inside over a whole length from a rear to a tip of the catheter 6, the fixed side optical fiber 1 is not rotated in the long catheter 6, and thus is not rubbed. Therefore, it is possible to prevent occurrences of rotation transmission delay, torque loss, and the like. In addition, the rotation side optical fiber 2 is rotatably disposed in a hole of the hollow rotating shaft 10 and an optical fiber guide bearing 8, and sliding loss is little.

Embodiment 5

Next, a description will be given of Embodiment 5 of a probe for 3D scanning-type optical imaging related to the invention using FIGS. 25 to 28.

Figure 25:
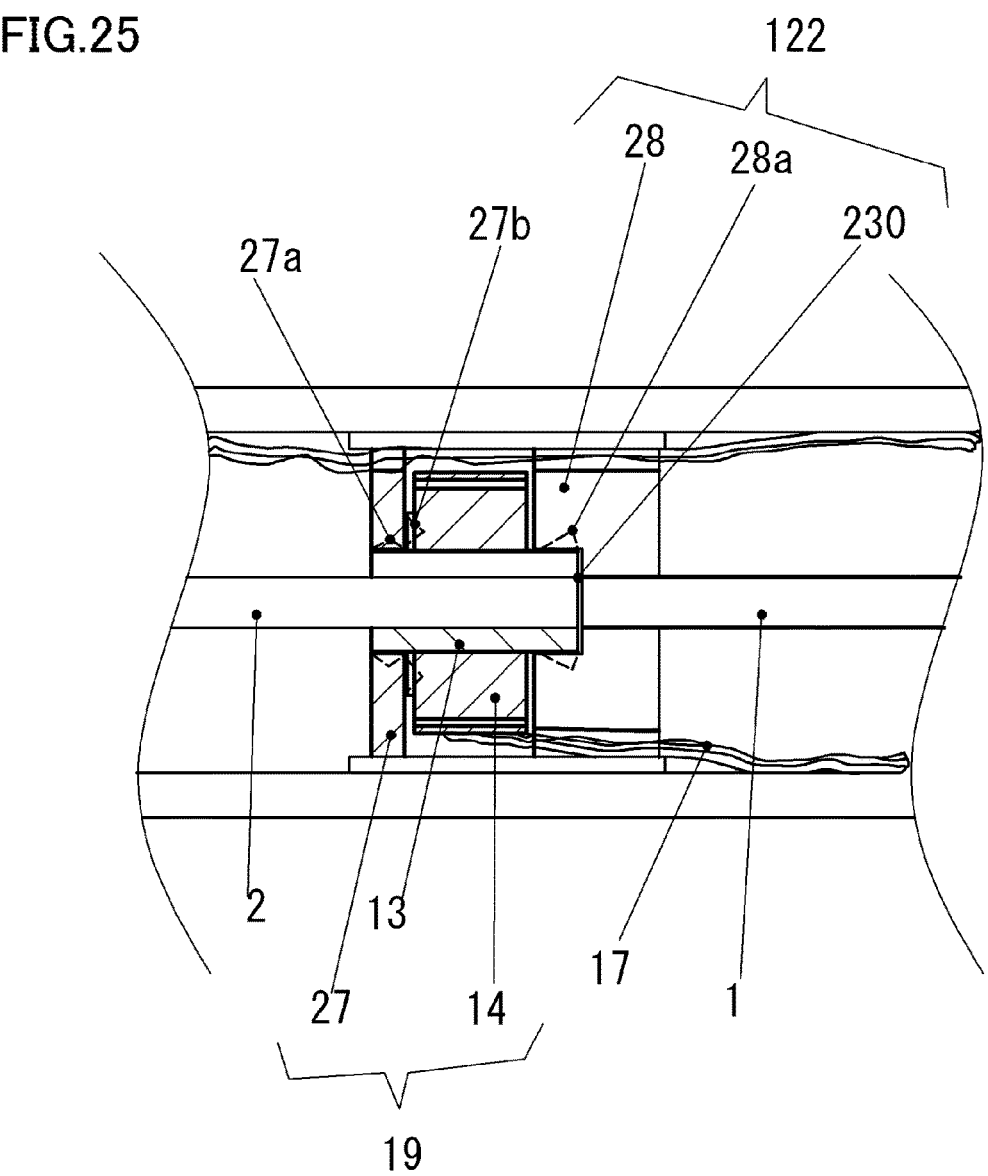
FIG. 25 is a cross-sectional view illustrating an optical rotary connector of a probe for optical imaging according to a fifth embodiment of the invention.

In the probe for 3D scanning-type optical imaging according to Embodiment 5 illustrated in FIG. 25, a rotation side optical fiber 2 and a fixed side optical fiber 1 having a length sufficient to connect a tip side to a rear side in a substantially tube-shaped catheter 6 have end surfaces processed smoothly in right angles and spaced apart with a gap less than or equal to about 100 μm [ideally less than or equal to 5 μm] to face each other on the same axis.

The rotation side optical fiber 2 integrally rotates with a second rotating shaft 13 of a second motor 19, and a position of a rotation center thereof is precisely regulated by a second front bearing 27 and a second rear bearing 28. In addition, the fixed side optical fiber 1 is fixed to the second rear bearing 28, and the precisely processed second rear bearing 28 maintains a concentricity of the fixed side optical fiber 1 and the rotation side optical fiber 2 at a high precision within several μm.

A transparent optical fluid 230 (for example, silicone oil, olefin oil, and a fluorine-based fluid having viscosity of 10 to 50 centistokes at room temperature) is injected into the gap between the fixed side optical fiber 1 and the rotation side optical fiber 2 of FIG. 25 as necessary. When a liquid is injected, an attenuation factor corresponding to a case, in which a light ray passes through between the fixed side optical fiber 1 and the rotation side optical fiber 2, decreases to about 1/10 thereof. Thus, an excellent light ray may be transmitted. In addition, even when the gap between the fixed side optical fiber 1 and the rotation side optical fiber 2 changes, the attenuation factor is not significantly degraded. Therefore, performance may be stabilized.

Figure 26:
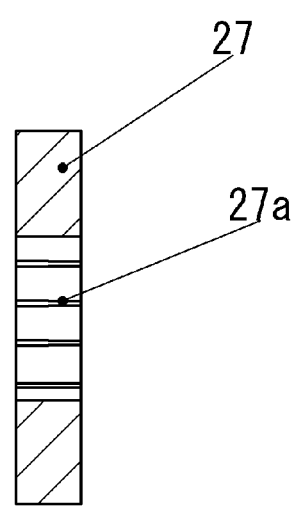
FIG. 26 is an enlarged view illustrating a first bearing of the probe for optical imaging.

For example, a dynamic pressure generating groove 15a having a straight pattern is provided on an inner peripheral surface of a bearing hole of a first bearing 15 illustrated in FIG. 26, and the dynamic pressure generating groove 15a applies a generated pressure to an optical fluid 18 flowing in. In this way, the second rotating shaft 13 emerges and rotates, and a rotation speed is smoothly maintained to reduce rotation speed unevenness. Moreover, it is possible to prevent rotational oscillation or rotational vibration from occurring, and maintain a positional precision of a rotation center at a high precision of about 1 μm or less.

Figure 27:
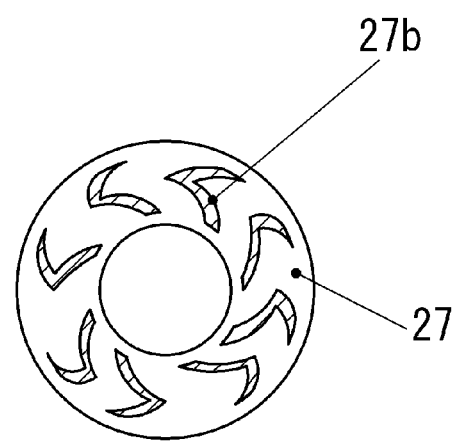
FIG. 27 is an enlarged view illustrating a first bearing of the probe for optical imaging.
Figure 28:
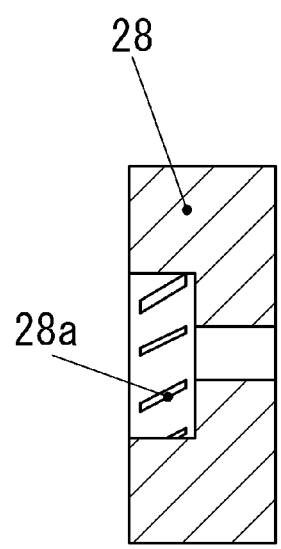
FIG. 28 is an enlarged view illustrating a second bearing of the probe for optical imaging.

Referring to FIG. 27, a dynamic pressure generating groove 27b having a fishbone pattern is provided on a surface where the second front bearing 27 and a side surface of the vibrator 14 face each other to generate a pressure in the axial direction in lubricating oil or the optical fluid 230 that flows in and create a gap in the axial direction for smooth rotation without contact. Additionally, position regulation is performed in the axial direction by creating a gap of a certain amount.

A dynamic pressure generating groove 28a having a screw groove pattern is processed on a bearing surface on which the second rotating shaft 13 of the second rear bearing 28 slides to generate a pressure in the optical fluid 230 flowing in on a bearing sliding surface, allow the second rotating shaft 13 to emerge, and smoothly maintain a rotation speed. Moreover, rotational oscillation or rotational vibration is prevented, and a favorable precision of a rotation position is maintained. In addition, the dynamic pressure generating groove 28a having the screw groove pattern is also effective in generating a seal pressure similarly to a screw pump by rotation, and functions as a fluid seal that confines the optical fluid 230 in the gap of the second rear bearing 28.

In addition, in order to avoid a risk that the optical fluid 230 confined in the gap of the second rear bearing 28 flows out or oozes out of a surface of the second bearing, the surface of the second bearing 28 is coated with a water repellent and oil repellent material containing a fluoride resin, and the like as necessary, and the optical fluid 230 is repelled, thereby preventing the optical fluid from oozing out.

In the present embodiment, the fixed side optical fiber 1 is not rotated in an inside of the long catheter 6 over a whole length from a rear to a tip of the catheter 6, and thus is not rubbed. Therefore, it is possible to prevent occurrences of rotation transmission delay, torque loss, and the like.

In addition, the rotation side optical fiber 2 is rotatably disposed in the hole of the hollow rotating shaft 1, and sliding loss is not present. Thus, rotational irregularity of the motor 12 is significantly small. In a general evaluation scale, performance of a speed of revolution is indicated by a percentage of a rotation angle. In the invention, it is possible to achieve high performance of 0.01%.

On the other hand, referring to rotational irregularity of a conventional endoscope probe using a scheme in which an optical fiber is rubbed, poor performance of about 100 times or more thereof has been obtained.

The most significant performance required from an OCT 3D manipulated image diagnosis apparatus of FIG. 8 is enhancement of spatial resolving power of a 3D image. Factors of enhancing spatial resolving power include rotation speed unevenness of the motor 12, runout accuracy of the hollow rotating shaft 10, accuracy and surface roughness of the first optical path conversion element 3 and the second optical path conversion means 20 and the like.

Among the factors, rotation speed unevenness of the motor 12 has great influence, and thus the endoscope probe of the invention that incorporates the motor 12 in a distal end portion and rotates an optical path conversion element at high accuracy and without rotation speed unevenness can stably achieve, for example, high 3D spatial resolving power of 10 μm or less.

According to the invention, an optical fiber is not relatively rotated in a catheter of an endoscope device or the like, and thus is not rubbed, and occurrences of rotation transmission delay, torque loss, and the like are reduced, thereby obtaining a clear OCT analyzed image at high spatial resolving power of 10 μm or less. In addition, when a thickness of a second optical path conversion means is intentionally changed, a light ray may be emitted in a certain range in an axial direction, and thus a 3D observation image may be obtained.

INDUSTRIAL APPLICABILITY

A probe for 3D scanning-type optical imaging of the invention may improve spatial resolving power corresponding to basic performance of an OCT image diagnosis apparatus to have spatial resolving power of about 10 μm or less without rotating an optical fiber in a long tube by providing an optical path conversion means that is rotated without uneven speed by a motor near a tip of the tube, thereby having a high-accuracy rotary scanner. Furthermore, it is possible to observe and diagnose a diseased part inside a human body by 3D scanning without conducting a surgical operation on the human body, and to achieve an elaborate diagnosis at a high resolution, which has not been achieved by X-ray CT, nuclear magnetic resonance or the like corresponding to a conventional diagnosis apparatus. In this way, the probe is particularly expected to be used for diagnosis and treatment of a microscopic lesion in a medical field, and applicable to an OCT diagnosis apparatus for industrial use in addition to an endoscope device for medical use.

EXPLANATIONS OF LETTERS OR NUMERALS

1 Fixed side optical fiber
2 Rotation side optical fiber
3a, 3b, 103a, 103b First optical path conversion means
4 Optical fiber fixture
5 Douser
6 Catheter (tube)
7, 107, 207 Motor coil
8, 108a, 108b, 208a, 208b Motor case
9a, 9b, 109a, 109b, 218a, 218b First bearing
10 Hollow rotating shaft
110 First rotating shaft
210 Second rotating shaft
11, 101, 201 Rotor magnet
12, 112, 219 First motor
13, 210 Second rotating shaft
14, 114, 214 Vibrator
14a Hole
14b Slit
15, 115, 215 Electrostrictive element
16, 116, 216 Pattern electrode
17, 23, 123, 223 Electric wire
18a, 18b, 18a, 18b, 209a, 209b Second bearing
19, 212 Second motor
20a, 20b, 120a, 220a, 320 Second optical path conversion means
21 Light-transmitting part
21a Spherical surface portion
22, 122, 222 Optical rotary connector
24, 24a, 24b Second pulse generating means
25, 25a, 25b First pulse generating means
26 Optical fiber guide bearing
27 Second front bearing
27a, 27b Dynamic pressure generating groove
28 Second rear bearing
28a Dynamic pressure generating groove
81 Forceps channel
82 Guide catheter
83 CCD camera unit
84 Distal end observation portion
85 Main body
86 First motor driver circuit
87 Second motor driver circuit
88 Optical interference analyzer
89 Computer
90 Monitor
124 Substantially flat portion
225 Substantially spherical surface portion
226 First cover
227 Second cover
228, 229 Barrier layer 230 Optical fluid
324 Reflecting surface

The invention claimed is:

1. A probe for optical imaging which guides light entering a tip side to a rear side, the probe comprising:
a non-rotatably disposed fixed side optical fiber incorporated in a substantially tube-shaped catheter;
a first optical path conversion means disposed on a tip side of the fixed side optical fiber and driven by a first motor to rotate, thereby emitting a light ray in a substantially radial direction;
a rotation side optical fiber positioned between the fixed side optical fiber and the first optical path conversion means, optically connected by an optical rotary connector, and driven by a second motor to rotate; and
a second optical path conversion means for rotating and emitting light by inclining an optical path to a tip side of the rotation side optical fiber by a minute angle with respect to a rotation center,
wherein the fixed side optical fiber, the first optical path conversion means, the rotation side optical fiber, and the second optical path conversion means are collinearly disposed.

2. The probe for optical imaging according to claim 1, wherein a rotating shaft of the first motor has a hollow shape, the first optical path conversion means is fixed thereto, and the rotation side optical fiber rotatably penetrates into a hollow hole, and
a rotating shaft of the second motor has a hollow shape, and the rotation side optical fiber is fixed to a hole corresponding to the hollow shape and rotated.

3. The probe for optical imaging according to claim 1, wherein the first optical path conversion means is fixed to the rotating shaft of the first motor, and the rotating shaft is positioned on a tip side with respect to the first optical path conversion means, and
the rotating shaft of the second motor has a hollow shape, and the rotation side optical fiber is fixed to a hole corresponding to the hollow shape and rotated.

4. The probe for optical imaging according to claim 1, wherein at least one of the first motor and the second motor is an ultrasonic motor using electrostrictive elements, the rotating shaft penetrates into a polygonal columnar center hole of a vibrator having the center hole, the center hole of the vibrator has a slit portion extending toward an outer circumference, a laminar electrostrictive element having an electrode is stuck to an outer peripheral surface of the vibrator, voltages are successively applied to the electrostrictive elements to generate rotational vibration in the vibrator, and the rotating shaft is driven to rotate.

5. The probe for optical imaging according to claim 1, wherein the first optical path conversion means is a rotatable mirror.

6. The probe for optical imaging according to claim 1, wherein the first optical path conversion means is a rotatable mirror, and a reflecting surface is a cylindrical surface.

7. The probe for optical imaging according to claim 1, wherein the second optical path conversion means is a prism having a substantially flat surface inclined to a tip.

8. The probe for optical imaging according to claim 1, wherein the second optical path conversion means is a prism having a substantially spherical surface inclined to a tip or a ball lens having a reflecting surface corresponding to a substantially flat surface in a portion of a substantially hemispheric shape.

9. The probe for optical imaging according to claim 1, wherein the optical rotary connector has a first cover covering an outer circumference of at least one of the fixed side optical fiber and the rotation side optical fiber with a minute gap interposed therebetween and a second cover covering the first cover with a minute gap interposed therebetween, a thread groove is formed on a cylindrical surface coming into contact with the minute gap of at least one of the first cover and the second cover, and a transparent fluid is injected into the minute gap.

10. The probe for optical imaging according to claim 1, wherein the optical rotary connector allows end surfaces of the fixed side optical fiber and the rotation side optical fiber to face each other with a minute distance therebetween, and injects a transparent fluid into a gap formed by the fixed side optical fiber, the rotation side optical fiber, a bearing of the second motor, and a rotating shaft of the second motor.

11. The probe for optical imaging according to claim 1, the probe further comprising:
a first pulse generating means for generating at least one pulse per rotation according to a rotation angle of the first motor, and a second pulse generating means for generating at least one pulse per rotation according to a rotation angle of the second motor; and
a control means for adjusting rotation speeds of the first motor and the second motor by pulses from the first pulse generating means and the second pulse generating means,
wherein the first motor and the second motor are rotated by setting a relation between a rotation speed N1 of the first motor and a rotation speed N2 of the second motor to N2=N1−X [rotations/second] such that a light ray is emitted in a substantially radial direction at a rotation speed of N1 [rotations/second] from the first optical path conversion means, and an emission angle of the light ray is changed in an axial direction at a speed of X [reciprocations/second].

12. The probe for optical imaging according to claim 1, wherein the first motor and the second motor are rotated at the same rotation speed by the control means by receiving pulses from the first pulse generating means and the second generating means such that the first motor and the second motor are in a stand-by state, and rotation per minute is changed by generation of a start signal such that a relation between the rotation speed N1 of the first motor and the rotation speed N2 of the second motor corresponds to N2=N1−X [rotations/second].

* * * * *